(12) United States Patent
Lipkens et al.

(10) Patent No.: US 11,377,651 B2
(45) Date of Patent: Jul. 5, 2022

(54) CELL THERAPY PROCESSES UTILIZING ACOUSTOPHORESIS

(71) Applicant: FloDesign Sonics, Inc., West Springfield, MA (US)

(72) Inventors: Bart Lipkens, Bloomfield, CT (US); Rui Tostoes, Northhampton, MA (US); Brian Dutra, East Longmeadow, MA (US); Rudolf Gilmanshin, Framingham, MA (US); Jason Dionne, Simsbury, CT (US); Walter M. Presz, Jr., Wilbraham, MA (US); Benjamin Ross-Johnsrud, Northhampton, MA (US); Goutam Ghoshal, East Grafton, MA (US); Kedar Chitale, Vernon, CT (US)

(73) Assignee: FloDesign Sonics, Inc., West Springfield, MA (US)

( * ) Notice: Subject to any disclaimer, the term of this patent is extended or adjusted under 35 U.S.C. 154(b) by 0 days.

(21) Appl. No.: 15/916,270

(22) Filed: Mar. 8, 2018

(65) Prior Publication Data

US 2019/0276815 A1 Sep. 12, 2019

Related U.S. Application Data

(63) Continuation-in-part of application No. 15/788,784, filed on Oct. 19, 2017.

(60) Provisional application No. 62/410,312, filed on Oct. 19, 2016, provisional application No. 62/468,895, filed on Mar. 8, 2017.

(51) Int. Cl.
*C12N 13/00* (2006.01)
*C12M 1/00* (2006.01)

(52) U.S. Cl.
CPC ............. *C12N 13/00* (2013.01); *C12M 23/14* (2013.01); *C12M 47/04* (2013.01)

(58) Field of Classification Search
CPC ............. G01N 30/76; G01N 33/54313; G01N 30/7293; G01N 30/462; G01N 2030/027; C07K 1/22; B01D 15/1807; B01D 15/3823; B01D 15/3866; C12N 13/00; C12M 35/04; C12M 47/04; C12M 23/14; C12M 23/42; C12M 23/44
See application file for complete search history.

(56) References Cited

U.S. PATENT DOCUMENTS 2,473,971 A 6/1949 Ross
2,535,355 A 12/1950 Froman
(Continued)

FOREIGN PATENT DOCUMENTS

AU 2002236405 9/2002
CN 105 087 788 A 11/2015
(Continued)

OTHER PUBLICATIONS

Lab on Chip, 2012, 12, 4296-4304 (Year: 2012).*
(Continued)

*Primary Examiner* — Shogo Sasaki
(74) *Attorney, Agent, or Firm* — FloDesign Sonics, Inc.

(57) ABSTRACT

A closed and modular fluidic system composed of one or more acoustic elements and cell processing reagents. The system employs a cellular manufacturing process for producing cell and gene therapy therapeutics.

10 Claims, 7 Drawing Sheets

(56) References Cited

U.S. PATENT DOCUMENTS

| | | |
|---|---|---|
| 2,667,944 A | 2/1954 | Crites |
| 3,004,338 A | 10/1961 | Turner |
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,125,789 A | 11/1978 | Van Schoiack |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,211,949 A | 7/1980 | Brisken et al. |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,484,907 A | 11/1984 | Sheeran, Jr. |
| 4,552,669 A | 11/1985 | Sekellick |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,860,993 A | 8/1989 | Goode |
| 4,878,210 A | 10/1989 | Mitome |
| 4,983,189 A | 1/1991 | Peterson et al. |
| 5,059,811 A | 10/1991 | King et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,562,823 A | 10/1996 | Reeves |
| 5,594,165 A | 1/1997 | Madanshetty |
| 5,604,301 A | 2/1997 | Mountford et al. |
| 5,626,767 A | 5/1997 | Trampier et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,844,140 A | 12/1998 | Seale et al. |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,029,518 A | 2/2000 | Oeftering |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,235,227 B2 | 6/2007 | Lanza et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,674,630 B2 | 3/2010 | Siversson |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,865,003 B2 | 10/2014 | Yang |
| 8,873,051 B2 | 10/2014 | Kaduchak et al. |
| 8,889,388 B2 | 11/2014 | Wang et al. |
| 9,023,658 B2 | 5/2015 | Gauer et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,375,662 B2 | 6/2016 | Kambayashi et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 9,532,769 B2 | 1/2017 | Dayton et al. |
| 9,533,241 B2 | 1/2017 | Presz, Jr. et al. |
| 9,550,134 B2 | 1/2017 | Lipkens et al. |
| 9,550,998 B2 | 1/2017 | Williams |
| 9,556,271 B2 | 1/2017 | Blumberg et al. |
| 9,556,411 B2 | 1/2017 | Lipkens et al. |
| 9,566,352 B2 | 2/2017 | Holmes et al. |
| 9,567,559 B2 | 2/2017 | Lipkens et al. |
| 9,567,609 B2 | 2/2017 | Paschon et al. |
| 9,572,897 B2 | 2/2017 | Bancel et al. |
| 9,573,995 B2 | 2/2017 | Schurpf et al. |
| 9,574,014 B2 | 2/2017 | Williams et al. |
| 9,580,500 B2 | 2/2017 | Schurpf et al. |

(56) References Cited

U.S. PATENT DOCUMENTS

| | | |
|---|---|---|
| 9,587,003 B2 | 3/2017 | Bancel et al. |
| 9,597,357 B2 | 3/2017 | Gregory et al. |
| 9,597,380 B2 | 3/2017 | Chakraborty et al. |
| 9,605,074 B2 | 3/2017 | Shah |
| 9,605,266 B2 | 3/2017 | Rossi et al. |
| 9,606,086 B2 | 3/2017 | Ding et al. |
| 9,608,547 B2 | 3/2017 | Ding et al. |
| 9,611,465 B2 | 4/2017 | Handa et al. |
| 9,616,090 B2 | 4/2017 | Conway et al. |
| 9,623,348 B2 | 4/2017 | McCarthy et al. |
| 9,629,877 B2 | 4/2017 | Cooper et al. |
| D787,630 S | 5/2017 | Lipkens et al. |
| 9,644,180 B2 | 5/2017 | Kahvejian et al. |
| 9,645,060 B2 | 5/2017 | Fiering |
| 9,656,263 B2 | 5/2017 | Laurell et al. |
| 9,657,290 B2 | 5/2017 | Dimov et al. |
| 9,662,375 B2 | 5/2017 | Jensen et al. |
| 9,663,756 B1 | 5/2017 | Lipkens et al. |
| 9,670,477 B2 | 6/2017 | Lipkens et al. |
| 9,670,938 B2 | 6/2017 | Beliavsky |
| 9,675,668 B2 | 6/2017 | Bancel et al. |
| 9,675,902 B2 | 6/2017 | Lipkens et al. |
| 9,675,906 B2 | 6/2017 | Lipkens et al. |
| 9,677,055 B2 | 6/2017 | Jones et al. |
| 9,685,155 B2 | 6/2017 | Hershey et al. |
| 9,686,096 B2 | 6/2017 | Lipkens et al. |
| 9,688,958 B2 | 6/2017 | Kennedy, III et al. |
| 9,689,234 B2 | 6/2017 | Gregory et al. |
| 9,689,802 B2 | 6/2017 | Caseres et al. |
| 9,695,063 B2 | 7/2017 | Rietman et al. |
| 9,695,442 B2 | 7/2017 | Guschin et al. |
| 9,810,665 B2 | 11/2017 | Fernald et al. |
| 9,833,763 B2 | 12/2017 | Fernald et al. |
| 9,869,618 B2 | 1/2018 | Hoyos et al. |
| 9,869,659 B2 | 1/2018 | Buckland et al. |
| 9,872,900 B2 | 1/2018 | Ciaramella et al. |
| 9,873,126 B2 | 1/2018 | Mao et al. |
| 9,873,894 B2 | 1/2018 | Conway et al. |
| 9,878,056 B2 | 1/2018 | Bancel et al. |
| 9,878,536 B2 | 1/2018 | Foresti et al. |
| 9,879,087 B2 | 1/2018 | DeSander et al. |
| 9,990,297 B2 | 1/2018 | Conway et al. |
| 9,907,846 B2 | 3/2018 | Morein et al. |
| 9,908,288 B2 | 3/2018 | Harkness |
| 9,909,117 B2 | 3/2018 | Kaduchak |
| 9,909,313 B1 | 3/2018 | Grubbs |
| 9,913,656 B2 | 3/2018 | Stulen |
| 9,913,866 B2 | 3/2018 | O'Shea et al. |
| 9,925,277 B2 | 3/2018 | Almarsson et al. |
| 9,926,382 B2 | 3/2018 | Fischer et al. |
| 9,937,207 B2 | 4/2018 | Gregory et al. |
| 9,938,390 B2 | 4/2018 | Storti et al. |
| 9,943,599 B2 | 4/2018 | Gehl et al. |
| 9,944,702 B2 | 4/2018 | Galetto |
| 9,944,709 B2 | 4/2018 | Galetto |
| 9,947,431 B2 | 4/2018 | El-zahab et al. |
| 9,994,743 B2 | 4/2018 | El-Zahab |
| 9,974,898 B2 | 5/2018 | Spain et al. |
| 9,983,459 B2 | 5/2018 | Arnold |
| 10,006,052 B2 | 6/2018 | Jarjour et al. |
| 10,045,913 B2 | 8/2018 | Warner et al. |
| 10,046,028 B2 | 8/2018 | Gregory et al. |
| 10,046,037 B2 | 8/2018 | Weinschenk et al. |
| 10,047,116 B2 | 8/2018 | Morein et al. |
| 10,047,123 B2 | 8/2018 | Weinschenk et al. |
| 10,047,124 B2 | 8/2018 | Weinschenk et al. |
| 10,047,144 B2 | 8/2018 | Elson et al. |
| 10,047,365 B2 | 8/2018 | Williams |
| 10,047,451 B2 | 8/2018 | Gaben et al. |
| 10,047,650 B2 | 8/2018 | Abram |
| 10,052,427 B2 | 8/2018 | Flieg et al. |
| 10,052,431 B2 | 8/2018 | Dreschel et al. |
| 10,052,631 B2 | 8/2018 | Ben-yakar et al. |
| 10,071,148 B2 | 9/2018 | Weinschenk et al. |
| 10,071,383 B2 | 9/2018 | Dionne et al. |
| 10,072,062 B2 | 9/2018 | Collingwood et al. |
| 10,073,098 B2 | 9/2018 | Wong et al. |
| 10,076,574 B2 | 9/2018 | Wang et al. |
| 10,160,786 B1 | 12/2018 | Weinschenk et al. |
| 10,166,255 B2 | 1/2019 | Moriarity et al. |
| 10,166,323 B2 | 1/2019 | Fiering et al. |
| 10,167,310 B2 | 1/2019 | Esteron |
| 10,167,474 B2 | 1/2019 | Rossi et al. |
| 10,167,478 B2 | 1/2019 | Williams |
| 10,175,240 B2 | 1/2019 | Mouchantat |
| 10,190,113 B2 | 1/2019 | Forsyth |
| 10,190,137 B2 | 1/2019 | Zhang et al. |
| 10,195,605 B2 | 2/2019 | Reinbigler et al. |
| 10,196,608 B2 | 2/2019 | Poirot et al. |
| 10,196,651 B2 | 2/2019 | Conway et al. |
| 10,196,652 B2 | 2/2019 | Conway et al. |
| 10,201,365 B2 | 2/2019 | Boudreaux et al. |
| 10,201,652 B2 | 2/2019 | Dutra et al. |
| 10,202,457 B2 | 2/2019 | Ruiz-opazo et al. |
| 10,202,762 B2 | 2/2019 | Sollohub et al. |
| 10,208,300 B2 | 2/2019 | Messina et al. |
| 10,214,013 B2 | 2/2019 | Foresti et al. |
| 10,214,718 B2 | 2/2019 | Berteau et al. |
| 10,215,760 B2 | 2/2019 | Grove |
| 10,221,843 B2 | 3/2019 | Locke et al. |
| 10,224,015 B2 | 3/2019 | Hsu |
| 10,236,797 B2 | 3/2019 | Wischnewskiy et al. |
| 10,238,365 B2 | 3/2019 | Shiraishi |
| 10,238,741 B2 | 3/2019 | Creusot |
| 10,239,058 B2 | 3/2019 | Lavieu et al. |
| 10,239,948 B2 | 3/2019 | Juillerat et al. |
| 10,245,064 B2 | 4/2019 | Rhee et al. |
| 10,251,664 B2 | 4/2019 | Shelton et al. |
| 10,253,296 B2 | 4/2019 | Kahvejian et al. |
| 10,254,212 B2 | 4/2019 | Ward et al. |
| 10,254,401 B2 | 4/2019 | Suyama |
| 10,258,698 B2 | 4/2019 | Hoge et al. |
| 10,261,078 B2 | 4/2019 | Branch et al. |
| 10,272,163 B2 | 4/2019 | Laterza et al. |
| 10,272,412 B2 | 4/2019 | Rubio Martinez et al. |
| 10,273,283 B2 | 4/2019 | Springer et al. |
| 10,286,007 B2 | 5/2019 | Galetto et al. |
| 10,308,928 B2 | 6/2019 | Lipkens et al. |
| 10,316,063 B1 | 6/2019 | Weinschenk et al. |
| 10,316,101 B2 | 6/2019 | Galetto |
| 10,322,949 B2 | 6/2019 | Lipkens et al. |
| 10,323,065 B1 | 6/2019 | Weinschenk et al. |
| 10,323,076 B2 | 6/2019 | Ellsworth et al. |
| 10,324,082 B2 | 6/2019 | Taylor et al. |
| 10,326,383 B2 | 6/2019 | Stiebel et al. |
| 10,334,390 B2 | 6/2019 | Bakish et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0057886 A1 | 3/2004 | Zumeris et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0055136 A1 | 3/2005 | Hofmann et al. |
| 2005/0121269 A1 | 6/2005 | Namduri |
| 2005/0145567 A1 | 7/2005 | Quintel et al. |
| 2005/0196725 A1 | 9/2005 | Fu |
| 2005/0239198 A1 | 10/2005 | Kunas |
| 2006/0037915 A1 | 2/2006 | Strand et al. |
| 2006/0037916 A1 | 2/2006 | Trampier |
| 2006/0050615 A1 | 3/2006 | Swisher |
| 2006/0257956 A1* | 11/2006 | Basset .............. G01N 33/54386 702/19 |
| 2007/0053795 A1 | 3/2007 | Laugharn et al. |
| 2007/0138108 A1 | 6/2007 | Hadfield et al. |
| 2007/0224676 A1 | 9/2007 | Haq |
| 2007/0267351 A1 | 11/2007 | Roach et al. |

(56) References Cited

U.S. PATENT DOCUMENTS

| | | |
|---|---|---|
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0042253 A1 | 2/2009 | Hiller et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0226994 A1 | 9/2009 | Lemor et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0006501 A1 | 1/2010 | Laurell et al. |
| 2010/0078323 A1 | 4/2010 | Takahashi et al. |
| 2010/0078384 A1* | 4/2010 | Yang ............... B01D 21/283 210/645 |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0071055 A1* | 3/2011 | Belgrader ......... B01L 3/502715 422/68.1 |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0207225 A1 | 8/2011 | Mehta et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0161903 A1 | 6/2012 | Thomas et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0206688 A1 | 8/2013 | El-Naas |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2013/0309757 A1 | 11/2013 | Kim |
| 2013/0316412 A1 | 11/2013 | Schultz |
| 2014/0011240 A1 | 1/2014 | Lipkens et al. |
| 2014/0017758 A1 | 1/2014 | Kniep et al. |
| 2014/0033808 A1 | 2/2014 | Ding et al. |
| 2014/0046181 A1 | 2/2014 | Benchimol et al. |
| 2014/0102947 A1 | 4/2014 | Baym et al. |
| 2014/0141413 A1 | 5/2014 | Laugham, Jr. et al. |
| 2014/0154795 A1 | 6/2014 | Lipkens et al. |
| 2014/0193381 A1 | 7/2014 | Warner et al. |
| 2014/0230912 A1 | 8/2014 | Aider et al. |
| 2014/0319077 A1 | 10/2014 | Lipkens et al. |
| 2014/0329997 A1 | 11/2014 | Kennedy, III et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0252317 A1 | 9/2015 | Lipkens et al. |
| 2015/0253226 A1 | 9/2015 | Augustsson et al. |
| 2015/0274550 A1 | 10/2015 | Lipkens et al. |
| 2015/0321129 A1 | 11/2015 | Lipkens et al. |
| 2015/0322397 A1* | 11/2015 | Cornforth ............... C12M 25/14 435/293.1 |
| 2016/0060615 A1 | 3/2016 | Walther et al. |
| 2016/0089620 A1 | 3/2016 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0139035 A1* | 5/2016 | Florescu .......... G01N 33/54326 506/40 |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0287778 A1 | 10/2016 | Leach et al. |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325039 A1 | 11/2016 | Leach et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2016/0368000 A1 | 12/2016 | Dionne et al. |
| 2016/0369236 A1 | 12/2016 | Kennedy, III |
| 2016/0370326 A9 | 12/2016 | Kaduchak et al. |
| 2017/0000413 A1 | 1/2017 | Clymer et al. |
| 2017/0002060 A1 | 1/2017 | Bolen et al. |
| 2017/0002839 A1 | 1/2017 | Burkland et al. |
| 2017/0007679 A1 | 1/2017 | Maeder et al. |
| 2017/0008029 A1 | 1/2017 | Lipkens et al. |
| 2017/0016025 A1 | 1/2017 | Poirot |
| 2017/0016027 A1 | 1/2017 | Lee et al. |
| 2017/0020926 A1 | 1/2017 | Mata-Fink et al. |
| 2017/0029802 A1 | 2/2017 | Lipkens et al. |
| 2017/0035866 A1 | 2/2017 | Poirot et al. |
| 2017/0037386 A1 | 2/2017 | Jones et al. |
| 2017/0038288 A1 | 2/2017 | Ward et al. |
| 2017/0042770 A1 | 2/2017 | Warner et al. |
| 2017/0044517 A1 | 2/2017 | Lipkens et al. |
| 2017/0049949 A1 | 2/2017 | Gilmanshin et al. |
| 2017/0056448 A1 | 3/2017 | Glick et al. |
| 2017/0058036 A1 | 3/2017 | Ruiz-Opazo et al. |
| 2017/0065636 A1 | 3/2017 | Moriarty et al. |

(56) References Cited

U.S. PATENT DOCUMENTS

| | | |
|---|---|---|
| 2017/0066015 A1 | 3/2017 | Lipkens et al. |
| 2017/0067021 A1 | 3/2017 | Moriarty et al. |
| 2017/0067022 A1 | 3/2017 | Poirot et al. |
| 2017/0072405 A1 | 3/2017 | Mao et al. |
| 2017/0073406 A1 | 3/2017 | Schurpf et al. |
| 2017/0073423 A1 | 3/2017 | Juillerat et al. |
| 2017/0073638 A1 | 3/2017 | Campana et al. |
| 2017/0073684 A1 | 3/2017 | Rossi et al. |
| 2017/0073685 A1 | 3/2017 | Maeder et al. |
| 2017/0080070 A1 | 3/2017 | Weinschenk et al. |
| 2017/0080423 A1 | 3/2017 | Dauson et al. |
| 2017/0081629 A1 | 3/2017 | Lipkens et al. |
| 2017/0088809 A1 | 3/2017 | Lipkens et al. |
| 2017/0088844 A1 | 3/2017 | Williams |
| 2017/0089826 A1 | 3/2017 | Lin |
| 2017/0096455 A1 | 4/2017 | Baric et al. |
| 2017/0107536 A1 | 4/2017 | Zhang et al. |
| 2017/0107539 A1 | 4/2017 | Yu et al. |
| 2017/0119820 A1 | 5/2017 | Moriarty et al. |
| 2017/0128523 A1 | 5/2017 | Ghatnekar et al. |
| 2017/0128857 A1 | 5/2017 | Lipkens et al. |
| 2017/0130200 A1 | 5/2017 | Moriarty et al. |
| 2017/0136168 A1 | 5/2017 | Spain et al. |
| 2017/0137491 A1 | 5/2017 | Matheson et al. |
| 2017/0137774 A1 | 5/2017 | Lipkens et al. |
| 2017/0137775 A1 | 5/2017 | Lipkens et al. |
| 2017/0137802 A1 | 5/2017 | Lipkens et al. |
| 2017/0145094 A1 | 5/2017 | Galetto |
| 2017/0151345 A1 | 6/2017 | Shah |
| 2017/0152502 A1 | 6/2017 | Scharenberg et al. |
| 2017/0152503 A1 | 6/2017 | Scharenberg et al. |
| 2017/0152504 A1 | 6/2017 | Scharenberg et al. |
| 2017/0152505 A1 | 6/2017 | Scharenberg et al. |
| 2017/0152527 A1 | 6/2017 | Paschon et al. |
| 2017/0152528 A1 | 6/2017 | Zhang et al. |
| 2017/0158749 A1 | 6/2017 | Cooper et al. |
| 2017/0159005 A1 | 6/2017 | Lipkens et al. |
| 2017/0159007 A1 | 6/2017 | Lipkens et al. |
| 2017/0166860 A1 | 6/2017 | Presz, Jr. et al. |
| 2017/0166877 A1 | 6/2017 | Bayle et al. |
| 2017/0166878 A9 | 6/2017 | Thanos et al. |
| 2017/0166903 A1 | 6/2017 | Zhang et al. |
| 2017/0173080 A1 | 6/2017 | Lee et al. |
| 2017/0173128 A1 | 6/2017 | Hoge et al. |
| 2017/0173498 A9 | 6/2017 | Lipkens et al. |
| 2017/0175073 A1 | 6/2017 | Lipkens et al. |
| 2017/0175125 A1 | 6/2017 | Welstead et al. |
| 2017/0175139 A1 | 6/2017 | Wu et al. |
| 2017/0175144 A1 | 6/2017 | Zhang et al. |
| 2017/0175509 A1 | 6/2017 | Abdel-Fattah et al. |
| 2017/0175720 A1 | 6/2017 | Tang et al. |
| 2017/0183390 A1 | 6/2017 | Springer et al. |
| 2017/0183413 A1 | 6/2017 | Galetto |
| 2017/0183418 A1 | 6/2017 | Galetto |
| 2017/0183420 A1 | 6/2017 | Gregory et al. |
| 2017/0184486 A1 | 6/2017 | Mach et al. |
| 2017/0184579 A1* | 6/2017 | Florescu ............... G01N 21/82 |
| 2017/0189450 A1 | 7/2017 | Conway et al. |
| 2017/0190767 A1 | 7/2017 | Schurpf et al. |
| 2017/0191022 A1 | 7/2017 | Lipkens et al. |
| 2017/0232439 A1 | 8/2017 | Suresh et al. |
| 2017/0260493 A1 | 9/2017 | Lipkens et al. |
| 2017/0291122 A1 | 10/2017 | Lipkens et al. |
| 2017/0374730 A1 | 12/2017 | Flores |
| 2018/0000311 A1 | 1/2018 | Lipkens et al. |
| 2018/0000870 A1 | 1/2018 | Britt |
| 2018/0000910 A1 | 1/2018 | Chakraborty et al. |
| 2018/0001011 A1 | 1/2018 | Paschon et al. |
| 2018/0008707 A1 | 1/2018 | Bussmer et al. |
| 2018/0009158 A1 | 1/2018 | Harkness et al. |
| 2018/0009888 A9 | 1/2018 | Baumeister et al. |
| 2018/0009895 A1 | 1/2018 | Smith et al. |
| 2018/0010085 A1 | 1/2018 | Lipkens et al. |
| 2018/0014846 A1 | 1/2018 | Rhee |
| 2018/0015128 A1 | 1/2018 | Britt |
| 2018/0015392 A1 | 1/2018 | Lipkens et al. |
| 2018/0016570 A1 | 1/2018 | Lipkens et al. |
| 2018/0016572 A1 | 1/2018 | Tang |
| 2018/0020295 A1 | 1/2018 | Pander et al. |
| 2018/0021379 A1 | 1/2018 | Galetto et al. |
| 2018/0022798 A1 | 1/2018 | Shurpf et al. |
| 2018/0028683 A1 | 2/2018 | Wong et al. |
| 2018/0043473 A1 | 2/2018 | Helvajian et al. |
| 2018/0049767 A1 | 2/2018 | Gee et al. |
| 2018/0051089 A1 | 2/2018 | Galetto et al. |
| 2018/0051265 A1 | 2/2018 | Cooper |
| 2018/0052095 A1 | 2/2018 | Cumbo et al. |
| 2018/0052147 A1 | 2/2018 | Zeng |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0055997 A1 | 3/2018 | Cabrera et al. |
| 2018/0056095 A1 | 3/2018 | Messerly et al. |
| 2018/0057810 A1 | 3/2018 | Zhang et al. |
| 2018/0058439 A1 | 3/2018 | Locke et al. |
| 2018/0066223 A1 | 3/2018 | Lim |
| 2018/0066224 A1 | 3/2018 | Lipkens et al. |
| 2018/0066242 A1 | 3/2018 | Zhang |
| 2018/0067044 A1 | 3/2018 | Kaduchak et al. |
| 2018/0071363 A1 | 3/2018 | Ghatnekar et al. |
| 2018/0071981 A1 | 3/2018 | Collino et al. |
| 2018/0078268 A1 | 3/2018 | Messerly |
| 2018/0080026 A1 | 3/2018 | Rossi et al. |
| 2018/0085743 A1 | 3/2018 | Yavorsky et al. |
| 2018/0087044 A1 | 3/2018 | Lipkens et al. |
| 2018/0088083 A1 | 3/2018 | Sinha |
| 2018/0092338 A1 | 4/2018 | Hering et al. |
| 2018/0092660 A1 | 4/2018 | Houser et al. |
| 2018/0094022 A1 | 4/2018 | Bracewell et al. |
| 2018/0095067 A1 | 4/2018 | Huff et al. |
| 2018/0098785 A1 | 4/2018 | Price et al. |
| 2018/0100134 A1 | 4/2018 | Lim |
| 2018/0100204 A1 | 4/2018 | O'Shea |
| 2018/0119174 A1 | 5/2018 | Scharenberg et al. |
| 2018/0130491 A1 | 5/2018 | Mathur |
| 2018/0136167 A1 | 5/2018 | Smith et al. |
| 2018/0143138 A1 | 5/2018 | Shreve et al. |
| 2018/0143167 A1 | 5/2018 | Mziray et al. |
| 2018/0147245 A1 | 5/2018 | O'shea et al. |
| 2018/0147576 A1 | 5/2018 | Lavieu et al. |
| 2018/0148740 A1 | 5/2018 | Conway et al. |
| 2018/0148763 A1 | 5/2018 | Shimada et al. |
| 2018/0153946 A1 | 6/2018 | Alemany et al. |
| 2018/0155716 A1 | 6/2018 | Zhang et al. |
| 2018/0157107 A1 | 6/2018 | Koyama et al. |
| 2018/0161775 A1 | 6/2018 | Kapur et al. |
| 2018/0177490 A1 | 6/2018 | Shiraishi |
| 2018/0178184 A1 | 6/2018 | Holland |
| 2018/0180610 A1 | 6/2018 | Taha et al. |
| 2018/0223256 A1 | 8/2018 | Kim |
| 2018/0223273 A1 | 8/2018 | Lipkens et al. |
| 2018/0223439 A1 | 8/2018 | Lipkens et al. |
| 2018/0230433 A1 | 8/2018 | Kokkaliaris et al. |
| 2018/0231555 A1 | 8/2018 | Davis |
| 2018/0236103 A1 | 8/2018 | Friedland et al. |
| 2018/0236280 A1 | 8/2018 | Cooke |
| 2018/0237533 A1 | 8/2018 | Juillerat et al. |
| 2018/0237768 A1 | 8/2018 | Reik et al. |
| 2018/0237798 A1 | 8/2018 | Duchateau et al. |
| 2018/0243382 A1 | 8/2018 | Wang et al. |
| 2018/0243665 A1 | 8/2018 | Lacki et al. |
| 2018/0244722 A1 | 8/2018 | Stickel et al. |
| 2018/0246103 A1 | 8/2018 | Lipkens et al. |
| 2018/0249688 A1 | 9/2018 | Ayares et al. |
| 2018/0250424 A1 | 9/2018 | Cotta-ramusino |
| 2018/0251723 A1* | 9/2018 | Murthy ............... C12M 41/14 |
| 2018/0251770 A1 | 9/2018 | Friedland et al. |
| 2018/0255751 A1 | 9/2018 | Regev et al. |
| 2018/0256922 A1 | 9/2018 | Mittelstein et al. |
| 2018/0257042 A1 | 9/2018 | Hester et al. |
| 2018/0257076 A1 | 9/2018 | Weitz et al. |
| 2018/0258160 A1 | 9/2018 | Lai et al. |
| 2018/0258955 A1 | 9/2018 | Levasseur et al. |

(56) References Cited

U.S. PATENT DOCUMENTS

| | | |
|---|---|---|
| 2018/0258957 A1 | 9/2018 | Levasseur et al. |
| 2018/0296954 A1 | 10/2018 | Trampler et al. |
| 2018/0353614 A1 | 12/2018 | Peters |
| 2018/0361053 A1 | 12/2018 | Fiering et al. |
| 2018/0361383 A1 | 12/2018 | Kapur et al. |
| 2018/0361384 A1 | 12/2018 | Kapur et al. |
| 2018/0369816 A1 | 12/2018 | Ai et al. |
| 2018/0371418 A1 | 12/2018 | Yang et al. |
| 2019/0000932 A1 | 1/2019 | Martini et al. |
| 2019/0000933 A1 | 1/2019 | Martini et al. |
| 2019/0000947 A1 | 1/2019 | Weinschenk et al. |
| 2019/0000959 A1 | 1/2019 | Ciaramella et al. |
| 2019/0000982 A1 | 1/2019 | Wang et al. |
| 2019/0002497 A1 | 1/2019 | Stickel et al. |
| 2019/0002504 A1 | 1/2019 | Weinschenk et al. |
| 2019/0002561 A1 | 1/2019 | Galetto |
| 2019/0002573 A1 | 1/2019 | Galetto |
| 2019/0002578 A1 | 1/2019 | Brayshaw et al. |
| 2019/0002589 A1 | 1/2019 | Bardroff et al. |
| 2019/0002890 A1 | 1/2019 | Martini et al. |
| 2019/0004052 A1 | 1/2019 | Herd et al. |
| 2019/0006036 A1 | 1/2019 | Jacobs et al. |
| 2019/0008943 A1 | 1/2019 | Poolman et al. |
| 2019/0008948 A1 | 1/2019 | Ciaramella et al. |
| 2019/0010190 A1 | 1/2019 | Weinschenk et al. |
| 2019/0010192 A1 | 1/2019 | Binder et al. |
| 2019/0010471 A1 | 1/2019 | Zhang et al. |
| 2019/0010495 A1 | 1/2019 | Boitano et al. |
| 2019/0010514 A1 | 1/2019 | Poirot et al. |
| 2019/0011407 A9 | 1/2019 | Lipkens et al. |
| 2019/0015501 A1 | 1/2019 | Ciaramella et al. |
| 2019/0016753 A1 | 1/2019 | Jang et al. |
| 2019/0016767 A1 | 1/2019 | Shah |
| 2019/0016781 A1 | 1/2019 | Bolen et al. |
| 2019/0022019 A1 | 1/2019 | Martini et al. |
| 2019/0023577 A1 | 1/2019 | Feng et al. |
| 2019/0024114 A1 | 1/2019 | Bauer et al. |
| 2019/0030073 A1 | 1/2019 | Kalayoglu et al. |
| 2019/0030151 A1 | 1/2019 | Jones et al. |
| 2019/0030533 A1 | 1/2019 | Shachar et al. |
| 2019/0031780 A1 | 1/2019 | Eavarone et al. |
| 2019/0031999 A1 | 1/2019 | Suresh et al. |
| 2019/0032036 A1 | 1/2019 | Zhang et al. |
| 2019/0032052 A1 | 1/2019 | Zhang et al. |
| 2019/0036152 A1 | 1/2019 | Gaben et al. |
| 2019/0036172 A1 | 1/2019 | Gaben et al. |
| 2019/0038671 A1 | 2/2019 | Fan et al. |
| 2019/0039060 A1 | 2/2019 | Chien et al. |
| 2019/0040099 A1 | 2/2019 | Brellisford et al. |
| 2019/0040117 A1 | 2/2019 | Elson et al. |
| 2019/0040414 A1 | 2/2019 | Wu |
| 2019/0046986 A1 | 2/2019 | Yuan et al. |
| 2019/0048060 A1 | 2/2019 | Conway et al. |
| 2019/0054112 A1 | 2/2019 | Gregoire |
| 2019/0054119 A1 | 2/2019 | Alma et al. |
| 2019/0054122 A1 | 2/2019 | Moriarity et al. |
| 2019/0055286 A1 | 2/2019 | Walz et al. |
| 2019/0055509 A1 | 2/2019 | Meacham et al. |
| 2019/0056302 A1 | 2/2019 | Berezin et al. |
| 2019/0056399 A1 | 2/2019 | Wong et al. |
| 2019/0060363 A1 | 2/2019 | Moriarity et al. |
| 2019/0062185 A1 | 2/2019 | Amouzadeh Tabrizi et al. |
| 2019/0062690 A1 | 2/2019 | Tostoes et al. |
| 2019/0062735 A1 | 2/2019 | Welstead et al. |
| 2019/0064146 A1 | 2/2019 | Glick et al. |
| 2019/0067554 A1 | 2/2019 | Karrai et al. |
| 2019/0070233 A1 | 3/2019 | Yeung et al. |
| 2019/0070528 A1 | 3/2019 | Luthe et al. |
| 2019/0071695 A1 | 3/2019 | Wagner et al. |
| 2019/0071717 A1 | 3/2019 | Zhang et al. |
| 2019/0076473 A1 | 3/2019 | Nguyen et al. |
| 2019/0076769 A1 | 3/2019 | Meacham et al. |
| 2019/0078133 A1 | 3/2019 | Cavanagh et al. |
| 2019/0079070 A1 | 3/2019 | Shiffman et al. |
| 2019/0083533 A1 | 3/2019 | Soon-shiong et al. |
| 2019/0085067 A1 | 3/2019 | Schurpf et al. |
| 2019/0085082 A1 | 3/2019 | Bicknell et al. |
| 2019/0085381 A1 | 3/2019 | Neely et al. |
| 2019/0090900 A1 | 3/2019 | Rhee et al. |
| 2019/0091683 A1 | 3/2019 | Baudoin et al. |
| 2019/0092794 A1 | 3/2019 | Rubio Martinez et al. |
| 2019/0092865 A1 | 3/2019 | Ruiz-opazo et al. |
| 2019/0093097 A1 | 3/2019 | Madison et al. |
| 2019/0094185 A1 | 3/2019 | Athanassiadis |
| 2019/0101541 A1 | 4/2019 | Wandall et al. |
| 2019/0105043 A1 | 4/2019 | Jaworek et al. |
| 2019/0106039 A1 | 4/2019 | Winton et al. |
| 2019/0106710 A1 | 4/2019 | Zhang et al. |
| 2019/0107420 A1 | 4/2019 | Kincel |
| 2019/0111480 A1 | 4/2019 | Barbati et al. |
| 2019/0119387 A1 | 4/2019 | Brett |
| 2019/0119701 A1 | 4/2019 | Liang et al. |
| 2019/0125839 A1 | 5/2019 | Frederick et al. |
| 2019/0127685 A1 | 5/2019 | Abdel Fattah et al. |
| 2019/0133633 A1 | 5/2019 | Neurohr et al. |
| 2019/0135942 A1 | 5/2019 | Duthe et al. |
| 2019/0136261 A1 | 5/2019 | Conway et al. |
| 2019/0143013 A1 | 5/2019 | Vincent et al. |
| 2019/0153027 A1 | 5/2019 | Natarajan et al. |
| 2019/0153106 A1 | 5/2019 | Ruiz-opazo et al. |
| 2019/0160463 A1 | 5/2019 | Ai et al. |
| 2019/0161540 A1 | 5/2019 | Gearing |
| 2019/0167722 A1 | 6/2019 | Soon-shiong et al. |
| 2019/0169233 A1 | 6/2019 | Weinschenk et al. |
| 2019/0169597 A1 | 6/2019 | Astrakhan et al. |
| 2019/0169639 A1 | 6/2019 | Zhang et al. |
| 2019/0170745 A1 | 6/2019 | Hu et al. |
| 2019/0173129 A1 | 6/2019 | Gaben et al. |
| 2019/0175517 A1 | 6/2019 | Martini et al. |
| 2019/0175651 A1 | 6/2019 | Lee et al. |
| 2019/0177368 A1 | 6/2019 | Weinschenk et al. |
| 2019/0177369 A1 | 6/2019 | Weinschenk et al. |
| 2019/0183931 A1 | 6/2019 | Alice et al. |
| 2019/0184035 A1 | 6/2019 | Jarjour et al. |
| 2019/0184312 A1 | 6/2019 | Liu et al. |
| 2019/0185860 A1 | 6/2019 | Kim et al. |
| 2019/0191252 A1 | 6/2019 | Lipkens et al. |
| 2019/0192653 A1 | 6/2019 | Hoge et al. |
| 2019/0194049 A1 | 6/2019 | Lindemann et al. |
| 2019/0194087 A1 | 6/2019 | Larsen |
| 2019/0194340 A1 | 6/2019 | Emtage et al. |
| 2019/0199312 A1 | 6/2019 | Dasgupta et al. |
| 2019/0199322 A1 | 6/2019 | Dasgupta et al. |
| 2021/0301459 A1* | 9/2021 | Haverhals ............... D06M 7/00 |
| 2021/0324318 A1* | 10/2021 | Parietti ................ C12M 41/40 |

FOREIGN PATENT DOCUMENTS

| | | |
|---|---|---|
| CN | 104722106 B | 4/2016 |
| DE | 30 27 433 A1 | 2/1982 |
| DE | 32 18 488 A1 | 11/1983 |
| DE | 196 48 519 A1 | 6/1998 |
| DE | 103 19 467 B3 | 7/2004 |
| DE | 10 2008 006 501 A1 | 9/2008 |
| DE | 102013224569 B3 | 6/2014 |
| DE | 10 2014 206 823 A1 | 10/2015 |
| EP | 0 292 470 B1 | 11/1988 |
| EP | 0 167 406 B1 | 7/1991 |
| EP | 0 641 606 | 3/1995 |
| EP | 1 175 931 A1 | 1/2002 |
| EP | 1 254 669 B1 | 11/2002 |
| EP | 1 308 724 A2 | 5/2003 |
| EP | 2 209 545 | 7/2010 |
| EP | 3219800 A1 | 9/2017 |
| EP | 270152 A1 | 1/2018 |
| EP | 2419511 | 1/2018 |
| EP | 3068888 | 1/2018 |
| EP | 3257600 | 1/2018 |
| EP | 3274453 | 1/2018 |
| EP | 3274454 | 1/2018 |
| EP | 3275894 | 1/2018 |
| EP | 278108 | 2/2018 |
| EP | 3279315 | 2/2018 |
| EP | 3286214 | 2/2018 |

(56) References Cited

FOREIGN PATENT DOCUMENTS

| | | |
|---|---|---|
| EP | 2289535 | 3/2018 |
| EP | 2545068 | 3/2018 |
| EP | 2675540 | 3/2018 |
| EP | 2750683 | 3/2018 |
| EP | 2796102 | 3/2018 |
| EP | 3066201 | 3/2018 |
| EP | 3066998 | 3/2018 |
| EP | 3107552 | 3/2018 |
| EP | 3288660 | 3/2018 |
| EP | 3288683 | 3/2018 |
| EP | 3289362 | 3/2018 |
| EP | 3291842 | 3/2018 |
| EP | 3291852 | 3/2018 |
| EP | 3292142 | 3/2018 |
| EP | 3292195 | 3/2018 |
| EP | 3292515 | 3/2018 |
| EP | 3294343 | 3/2018 |
| EP | 3294764 | 3/2018 |
| EP | 3294857 | 3/2018 |
| EP | 3294871 | 3/2018 |
| EP | 3294888 | 3/2018 |
| EP | 3294896 | 3/2018 |
| EP | 3296302 | 3/2018 |
| EP | 3297740 | 3/2018 |
| EP | 3298046 | 3/2018 |
| EP | 3164488 | 4/2018 |
| EP | 3301115 | 4/2018 |
| EP | 3302783 | 4/2018 |
| EP | 3302789 | 4/2018 |
| EP | 3303558 | 4/2018 |
| EP | 3306310 | 4/2018 |
| EP | 2675901 B1 | 5/2018 |
| EP | 2956772 B1 | 5/2018 |
| EP | 3323444 A1 | 5/2018 |
| EP | 3324996 A2 | 5/2018 |
| EP | 3327127 A1 | 5/2018 |
| EP | 3337819 A2 | 6/2018 |
| EP | 2772196 B1 | 8/2018 |
| EP | 2882091 B1 | 8/2018 |
| EP | 2910568 B1 | 8/2018 |
| EP | 3265805 A4 | 8/2018 |
| EP | 3359676 A1 | 8/2018 |
| EP | 3360955 A1 | 8/2018 |
| EP | 3361252 A1 | 8/2018 |
| EP | 3362102 A1 | 8/2018 |
| EP | 3363456 A1 | 8/2018 |
| EP | 3363813 A1 | 8/2018 |
| EP | 3365062 A1 | 8/2018 |
| EP | 3365095 A1 | 8/2018 |
| EP | 3365441 A1 | 8/2018 |
| EP | 3365447 A1 | 8/2018 |
| EP | 3366696 A1 | 8/2018 |
| EP | 3367118 A2 | 8/2018 |
| EP | 2931892 B1 | 9/2018 |
| EP | 3019606 B1 | 9/2018 |
| EP | 3089800 A4 | 9/2018 |
| EP | 3123534 B1 | 9/2018 |
| EP | 3368528 A1 | 9/2018 |
| EP | 3368670 A1 | 9/2018 |
| EP | 3371295 A1 | 9/2018 |
| EP | 3372813 A1 | 9/2018 |
| EP | 3372814 A1 | 9/2018 |
| EP | 2922902 B1 | 1/2019 |
| EP | 3421975 A1 | 1/2019 |
| EP | 3423092 A1 | 1/2019 |
| EP | 3423580 A1 | 1/2019 |
| EP | 3425386 A1 | 1/2019 |
| EP | 3426271 A1 | 1/2019 |
| EP | 3426372 A1 | 1/2019 |
| EP | 3426375 A2 | 1/2019 |
| EP | 3426690 A1 | 1/2019 |
| EP | 3427815 A1 | 1/2019 |
| EP | 3429753 A1 | 1/2019 |
| EP | 3430050 A1 | 1/2019 |
| EP | 3430134 A1 | 1/2019 |
| EP | 3430146 A1 | 1/2019 |
| EP | 3430463 A1 | 1/2019 |
| EP | 3433363 A1 | 1/2019 |
| EP | 3433366 A1 | 1/2019 |
| EP | 3434774 A1 | 1/2019 |
| EP | 3434776 A1 | 1/2019 |
| EP | 2598533 B1 | 2/2019 |
| EP | 2691422 B1 | 2/2019 |
| EP | 2925431 B1 | 2/2019 |
| EP | 3170185 B1 | 2/2019 |
| EP | 3436030 A1 | 2/2019 |
| EP | 3436196 A2 | 2/2019 |
| EP | 3436575 A1 | 2/2019 |
| EP | 3436579 A1 | 2/2019 |
| EP | 3437740 A1 | 2/2019 |
| EP | 3439698 A1 | 2/2019 |
| EP | 3440191 A1 | 2/2019 |
| EP | 3441468 A2 | 2/2019 |
| EP | 3442598 A2 | 2/2019 |
| EP | 3443002 A1 | 2/2019 |
| EP | 3443084 A2 | 2/2019 |
| EP | 3445407 A1 | 2/2019 |
| EP | 3445848 A1 | 2/2019 |
| EP | 3445853 A1 | 2/2019 |
| EP | 3445856 A1 | 2/2019 |
| EP | 2694091 B1 | 3/2019 |
| EP | 3080260 B1 | 3/2019 |
| EP | 3448291 A1 | 3/2019 |
| EP | 3448995 A1 | 3/2019 |
| EP | 3449850 A1 | 3/2019 |
| EP | 3452133 A1 | 3/2019 |
| EP | 3452499 A2 | 3/2019 |
| EP | 3453406 A1 | 3/2019 |
| EP | 3456339 A2 | 3/2019 |
| EP | 3458081 A1 | 3/2019 |
| EP | 3458083 A1 | 3/2019 |
| EP | 3458104 A1 | 3/2019 |
| EP | 3458105 A1 | 3/2019 |
| EP | 3458107 A1 | 3/2019 |
| EP | 3458108 A1 | 3/2019 |
| EP | 3458590 A1 | 3/2019 |
| EP | 3066115 B1 | 4/2019 |
| EP | 3119807 B1 | 4/2019 |
| EP | 3186281 B1 | 4/2019 |
| EP | 3463433 A1 | 4/2019 |
| EP | 3463660 A1 | 4/2019 |
| EP | 3464198 A1 | 4/2019 |
| EP | 3464594 A1 | 4/2019 |
| EP | 3467276 A1 | 4/2019 |
| EP | 3467491 A1 | 4/2019 |
| EP | 3468225 A1 | 4/2019 |
| EP | 3468351 A1 | 4/2019 |
| EP | 3468594 A1 | 4/2019 |
| EP | 3470089 A1 | 4/2019 |
| EP | 3470519 A1 | 4/2019 |
| EP | 3471621 A1 | 4/2019 |
| EP | 3473707 A1 | 4/2019 |
| EP | 2546144 B1 | 5/2019 |
| EP | 3311588 B1 | 5/2019 |
| EP | 3474904 A1 | 5/2019 |
| EP | 3475307 A1 | 5/2019 |
| EP | 3481361 A1 | 5/2019 |
| EP | 3481867 A1 | 5/2019 |
| EP | 2412817 B2 | 6/2019 |
| EP | 3490562 A1 | 6/2019 |
| EP | 3490574 A1 | 6/2019 |
| EP | 3490694 A1 | 6/2019 |
| EP | 3490712 A1 | 6/2019 |
| EP | 3491124 A1 | 6/2019 |
| EP | 3491126 A1 | 6/2019 |
| EP | 3493836 A1 | 6/2019 |
| EP | 3493907 A1 | 6/2019 |
| EP | 3495376 A1 | 6/2019 |
| EP | 3495811 A1 | 6/2019 |
| EP | 3498846 A1 | 6/2019 |
| EP | 3500244 A1 | 6/2019 |
| EP | 3500271 A1 | 6/2019 |
| EP | 3500297 A1 | 6/2019 |
| EP | 3500659 A1 | 6/2019 |

(56) References Cited

FOREIGN PATENT DOCUMENTS

| | | |
|---|---|---|
| EP | 3500696 A1 | 6/2019 |
| EP | 3502137 A1 | 6/2019 |
| EP | 3502253 A1 | 6/2019 |
| EP | 3490801 B1 | 6/2021 |
| GB | 2 420 510 A | 5/2006 |
| JP | 2-290266 A | 11/1990 |
| JP | 9-136090 | 5/1997 |
| JP | 11-90110 A | 4/1999 |
| JP | 2005-249267 A | 9/2005 |
| KR | 1442486 | 9/2014 |
| RU | 2037327 C1 | 6/1995 |
| RU | 94015846 A | 6/1996 |
| RU | 2067079 C1 | 9/1996 |
| RU | 2085933 | 7/1997 |
| SU | 629496 | 10/1978 |
| WO | WO 1987/07178 A1 | 12/1987 |
| WO | WO 89/11899 A1 | 12/1989 |
| WO | WO 90/05008 | 3/1990 |
| WO | WO 95/01214 A1 | 1/1995 |
| WO | WO 97/34643 | 9/1997 |
| WO | WO 1998/017373 | 4/1998 |
| WO | WO 98/50133 A1 | 11/1998 |
| WO | WO 00/41794 | 7/2000 |
| WO | WO 02/072234 A1 | 9/2002 |
| WO | WO 02/072236 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | 2011/130321 A2 | 10/2011 |
| WO | WO 2011/131947 A2 | 10/2011 |
| WO | WO 2011/161463 A2 | 12/2011 |
| WO | 2013/030691 A2 | 3/2013 |
| WO | 2013/043046 A1 | 3/2013 |
| WO | WO 2013/043044 A1 | 3/2013 |
| WO | WO 2013/043297 A1 | 3/2013 |
| WO | WO 2013/049623 A1 | 4/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | 2014/035457 A1 | 3/2014 |
| WO | WO 2014/046605 A1 | 3/2014 |
| WO | WO 2014/055219 A2 | 4/2014 |
| WO | 2014/083162 A2 | 6/2014 |
| WO | WO 2014/124306 A1 | 8/2014 |
| WO | 2014/165177 A1 | 10/2014 |
| WO | WO 2014/153651 | 10/2014 |
| WO | WO 2015/006730 | 1/2015 |
| WO | WO 2015/102528 | 7/2015 |
| WO | 2015/144135 A1 | 10/2015 |
| WO | WO 2016/004398 A2 | 1/2016 |
| WO | WO 2016/124542 | 8/2016 |
| WO | 2016/141204 A1 | 9/2016 |
| WO | WO 2016/176663 | 11/2016 |
| WO | 2016/205749 A1 | 12/2016 |
| WO | 2016/205764 A1 | 12/2016 |
| WO | WO 2016/209082 | 12/2016 |
| WO | 2017/011519 A1 | 1/2017 |
| WO | 2017/015622 A2 | 1/2017 |
| WO | 2017/021543 A1 | 2/2017 |
| WO | 2017/031476 A2 | 2/2017 |
| WO | WO 2017/041102 | 3/2017 |
| WO | 2017/066707 A1 | 4/2017 |
| WO | 2017/069965 A1 | 4/2017 |
| WO | 2017/070110 A1 | 4/2017 |
| WO | 2017/070284 A1 | 4/2017 |
| WO | 2017/070605 A1 | 4/2017 |
| WO | 2017/072131 A1 | 5/2017 |
| WO | 2017/075475 A1 | 5/2017 |
| WO | 2017/079674 A1 | 5/2017 |
| WO | 2017/101749 A1 | 6/2017 |
| WO | 2017/148928 A1 | 9/2017 |
| WO | 2017/152015 A1 | 9/2017 |
| WO | 2017/153038 A2 | 9/2017 |
| WO | 2017/156349 A1 | 9/2017 |
| WO | 2017/156484 A1 | 9/2017 |
| WO | 2017/157426 A1 | 9/2017 |
| WO | 2017/158339 A1 | 9/2017 |
| WO | 2017/160991 A1 | 9/2017 |
| WO | 2017/161384 A1 | 9/2017 |
| WO | 2017/161553 A1 | 9/2017 |
| WO | 2017/165826 A1 | 9/2017 |
| WO | 2017/172645 A2 | 10/2017 |
| WO | 2017/173005 A1 | 10/2017 |
| WO | 2017/173384 A1 | 10/2017 |
| WO | 2017/175145 A1 | 10/2017 |
| WO | 2017/177137 A1 | 10/2017 |
| WO | 2017/178354 A1 | 10/2017 |
| WO | 2017/180665 A2 | 10/2017 |
| WO | 2017/180786 A2 | 10/2017 |
| WO | 2017/180993 A1 | 10/2017 |
| WO | 2017/184768 A1 | 10/2017 |
| WO | 2017/186718 A1 | 11/2017 |
| WO | 2017/189308 A1 | 11/2017 |
| WO | 2017/191289 A1 | 11/2017 |
| WO | 2017/192760 A1 | 11/2017 |
| WO | 2017/193107 A2 | 11/2017 |
| WO | 2017/201328 A1 | 11/2017 |
| WO | 2017/201342 A1 | 11/2017 |
| WO | 2017/201346 A1 | 11/2017 |
| WO | 2017/201347 A1 | 11/2017 |
| WO | 2017/201348 A1 | 11/2017 |
| WO | 2017/201350 A1 | 11/2017 |
| WO | 2017/202747 A1 | 11/2017 |
| WO | 2017/202949 A1 | 11/2017 |
| WO | WO 20174201349 | 11/2017 |
| WO | 2017/207589 A1 | 12/2017 |
| WO | 2017/214216 A1 | 12/2017 |
| WO | 2017/217870 A1 | 12/2017 |
| WO | 2017/218519 A1 | 12/2017 |
| WO | 2017/220767 A1 | 12/2017 |
| WO | 2017/222777 A1 | 12/2017 |
| WO | WO 2017218714 | 12/2017 |
| WO | WO 2018/009894 A1 | 1/2018 |
| WO | WO 2018002036 | 1/2018 |
| WO | WO 2018005873 | 1/2018 |
| WO | WO 2018013558 | 1/2018 |
| WO | WO 2018013629 A1 | 1/2018 |
| WO | WO 2018013840 | 1/2018 |
| WO | WO2018014174 | 1/2018 |
| WO | WO2018015561 | 1/2018 |
| WO | WO 20180011600 | 1/2018 |
| WO | 2018/026605 A1 | 2/2018 |
| WO | 2018/026914 A1 | 2/2018 |
| WO | WO2018018958 | 2/2018 |
| WO | WO2018021920 | 2/2018 |
| WO | WO2018022158 | 2/2018 |
| WO | WO 2018022513 | 2/2018 |
| WO | WO2018022619 | 2/2018 |
| WO | WO2018022651 | 2/2018 |
| WO | WO2018022930 | 2/2018 |
| WO | WO2018023114 | 2/2018 |
| WO | WO2018024639 | 2/2018 |
| WO | WO2018026644 | 2/2018 |
| WO | WO2018026941 | 2/2018 |
| WO | WO2018028647 | 2/2018 |
| WO | WO 2018034343 | 2/2018 |
| WO | WO2018034885 | 2/2018 |
| WO | WO 2018035141 | 2/2018 |
| WO | WO 2018035423 | 2/2018 |
| WO | WO2018020269I | 2/2018 |
| WO | WO2018034655 | 3/2018 |
| WO | WO 2018038711 | 3/2018 |
| WO | WO 2018039119 | 3/2018 |
| WO | WO 2018039407 | 3/2018 |

(56) References Cited

FOREIGN PATENT DOCUMENTS

| | | |
|---|---|---|
| WO | WO 2018039408 | 3/2018 |
| WO | WO 2018039410 | 3/2018 |
| WO | WO 2018039412 | 3/2018 |
| WO | WO 2018039515 | 3/2018 |
| WO | WO 2018045284 | 3/2018 |
| WO | WO 2018049226 | 3/2018 |
| WO | WO 2018050738 | 3/2018 |
| WO | WO 2018057825 | 3/2018 |
| WO | 2018/058275 A1 | 4/2018 |
| WO | WO 2018063291 | 4/2018 |
| WO | 2018/091879 A1 | 5/2018 |
| WO | 2018/094244 A1 | 5/2018 |
| WO | WO 2018081476 | 5/2018 |
| WO | WO 2018081476 | 5/2018 |
| WO | WO 2018081476 | 5/2018 |
| WO | 2018/098671 A1 | 6/2018 |
| WO | 2018/102752 A1 | 6/2018 |
| WO | 2018/106163 A1 | 6/2018 |
| WO | 2018/112145 A1 | 6/2018 |
| WO | 2018/112335 A1 | 6/2018 |
| WO | 2018/138385 A1 | 8/2018 |
| WO | 2018/140573 A1 | 8/2018 |
| WO | 2018/140845 A2 | 8/2018 |
| WO | 2018/142364 A1 | 8/2018 |
| WO | 2018/151811 A2 | 8/2018 |
| WO | 2018/151823 A1 | 8/2018 |
| WO | 2018/153772 A1 | 8/2018 |
| WO | 2018/160548 A1 | 9/2018 |
| WO | 2018/160909 A1 | 9/2018 |
| WO | 2018/160993 A1 | 9/2018 |
| WO | 2018/161017 A1 | 9/2018 |
| WO | 2018/161026 A1 | 9/2018 |
| WO | 2018/161038 A1 | 9/2018 |
| WO | 2018/161905 A1 | 9/2018 |
| WO | 2018/163183 A1 | 9/2018 |
| WO | 2018/227286 A1 | 12/2018 |
| WO | 2018/229612 A1 | 12/2018 |
| WO | 2018/231759 A1 | 12/2018 |
| WO | 2018/231990 A2 | 12/2018 |
| WO | 2018/232045 A1 | 12/2018 |
| WO | 2018/232131 A1 | 12/2018 |
| WO | 2018/234421 A1 | 12/2018 |
| WO | 2018/235228 A1 | 12/2018 |
| WO | 2018/236708 A1 | 12/2018 |
| WO | 2018/237201 A1 | 12/2018 |
| WO | 2018/237239 A1 | 12/2018 |
| WO | 2018/183966 A3 | 1/2019 |
| WO | 2019/002551 A1 | 1/2019 |
| WO | 2019/002633 A1 | 1/2019 |
| WO | 2019/005155 A1 | 1/2019 |
| WO | 2019/007869 A1 | 1/2019 |
| WO | 2019/008335 A1 | 1/2019 |
| WO | 2019/010422 A1 | 1/2019 |
| WO | 2019/018423 A1 | 1/2019 |
| WO | 2019/018491 A1 | 1/2019 |
| WO | 2019/018796 A1 | 1/2019 |
| WO | 2019/022671 A1 | 1/2019 |
| WO | 2019/023523 A1 | 1/2019 |
| WO | 2019/025661 A1 | 2/2019 |
| WO | 2019/025984 A1 | 2/2019 |
| WO | 2019/028172 A1 | 2/2019 |
| WO | 2019/032675 A1 | 2/2019 |
| WO | 2019/036382 A1 | 2/2019 |
| WO | 2019/041344 A1 | 3/2019 |
| WO | 2019/046450 A1 | 3/2019 |
| WO | 2019/048639 A1 | 3/2019 |
| WO | 2019/048666 A1 | 3/2019 |
| WO | 2019/051106 A1 | 3/2019 |
| WO | 2019/051255 A1 | 3/2019 |
| WO | 2019/051278 A1 | 3/2019 |
| WO | 2019/051316 A1 | 3/2019 |
| WO | 2019/051355 A1 | 3/2019 |
| WO | 2019/055697 A1 | 3/2019 |
| WO | 2019/055817 A1 | 3/2019 |
| WO | 2019/055896 A1 | 3/2019 |
| WO | 2019/056015 A2 | 3/2019 |
| WO | 2019/057774 A1 | 3/2019 |
| WO | 2019/058321 A1 | 3/2019 |
| WO | 2019/058326 A1 | 3/2019 |
| WO | 2019/060253 A1 | 3/2019 |
| WO | 2019/060425 A1 | 3/2019 |
| WO | 2019/060779 A1 | 3/2019 |
| WO | 2019/067015 A1 | 4/2019 |
| WO | 2019/069101 A1 | 4/2019 |
| WO | 2019/070541 A1 | 4/2019 |
| WO | 2019/070974 A1 | 4/2019 |
| WO | 2019/072889 A1 | 4/2019 |
| WO | 2019/075409 A1 | 4/2019 |
| WO | 2019/079497 A1 | 4/2019 |
| WO | 2019/079819 A1 | 4/2019 |
| WO | 2019/080898 A1 | 5/2019 |
| WO | 2019/081521 A1 | 5/2019 |
| WO | 2019/094360 A1 | 5/2019 |
| WO | 2019/098839 A1 | 5/2019 |
| WO | 2019/099619 A1 | 5/2019 |
| WO | 2019/099736 A1 | 5/2019 |
| WO | 2019/099949 A1 | 5/2019 |
| WO | 2019/101691 A1 | 5/2019 |
| WO | 2019/101956 A1 | 5/2019 |
| WO | 2018/215686 A9 | 6/2019 |
| WO | 2019/111250 A1 | 6/2019 |
| WO | 2019/113310 A1 | 6/2019 |
| WO | 2019/118475 A1 | 6/2019 |

OTHER PUBLICATIONS

Fiering et al. SLAS Technology 2018, vol. 23 (4) 352-363. (Year: 2018).*
Borenstein et al. Eurpoena Pharmaceutical Review Website Jun. 29, 2017. (Year: 2017).*
Bancroft et al. Biopharma reporter Website Feb. 7, 2017. (Year: 2017).*
Alvarez et al.; ShockWaves, vol. 17, No. 6, pp. 441-447, 2008.
Augustsson et al., Acoustophoretic microfluidic chip for sequential elution of surface bound molecules from beads or cells, Biomicrofluidics, Sep. 2012, 6(3):34115.
Benes et al.; Ultrasonic Separation of Suspended Particles, 2001 IEEE Ultrasonics Symposium; Oct. 7-10, 2001; pp. 649-659; Atlanta, Georgia.
Castilho et al.; Animal Cell Technology: From Biopharmaceuticals to Gene Therapy; 11—Animal Cell Separation; 2008.
Castro; Tunable gap and quantum quench dynamics in bilayer graphene; Jul. 13, 2010; Mathematica Summer School.
Chitale et al.; Understanding the Fluid Dynamics Associated with Macro Scale Ultrasonic Separators; Proceedings of Meetings on Acoustics, May 2015.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Grenvall et al.; Concurrent Isolation of Lymphocytes and Granulocytes Using Prefocused Free Flow Acoustophoresis; Analytical Chemistry; vol. 87; pp. 5596-5604; 2015.
Higginson et al.; Tunable optics derived from nonlinear acoustic effects; Journal of Applied Physics; vol. 95; No. 10; pp. 5896-5904; 2004.
Hill et al.; Ultrasonic Particle Manipulation; Microfluidic Technologies for Miniaturized Analysis Systems, Jan. 2007, pp. 359-378.
Ilinskii et al.; Acoustic Radiation Force on a Sphere in Tissue; AIP Conference Proceedings; 2012.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.

(56) References Cited

OTHER PUBLICATIONS

Li et al.; Electromechanical behavior of PZT-brass unimorphs; J. Am. Ceram. Soc. vol. 82; No. 7; pp. 1733-1740, 1999.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; Separation of bacterial spores from flowering water in macro-scale cavities by ultrasonic standing waves; submitted/ uploaded to http://arxiv.org/abs/1006.5467 on Jun. 28, 2010.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et al.; An Industrial-Prototype Acoustic Array for Real-Time Emulsion Layer Detection in Oil Storage Tanks; IEEE Sensors Journal, vol. 9, No. 12, Dec. 2009.
Musiak et al.; Design of a Control System for Acoustophoretic Separation, 2013 IEEE 56$^{th}$ International Midwest Symposium on Circuits and Systems (MWSCAS), Aug. 2013, pp. 1120-1123.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
phys. org. "Engineers develop revolutionary nanotech water desalination membrane." Nov. 6, 2006. http://phys.org/news82047372.html.
Ponomarenko et al.; Density of states and zero Landau level probed through capacitance of graphene; Nature Nanotechnology Letters, Jul. 5, 2009; DOI: 10.1038/NNANO.2009.177.
"Proceedings of the Acoustics 2012 Nantes Conference," Apr. 23-27, 2012, Nantes, France, pp. 278-282.
Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.
Seymour et al, J. Chem. Edu., 1990, 67(9), p. 763, published Sep. 1990.
Volpin et al.; Mesh simplification with smooth surface reconstruction; Computer-Aided Design; vol. 30; No. 11; 1998.
Wang et al.; Retention and Viability Characteristics of Mammalian Cells in an Acoustically Driven Polymer Mesh; Biotechnol. Prog. 2004, pp. 384-387 (2004).
Wicklund et al.; Ultrasonic Manipulation of Single Cells; Methods in Molecular Biology; vol. 853; pp. 1777-196; 2012.
Annex to Form PCT/ISA/206—Communication Relating to the Results of the Partial International Search Report dated Jul. 18, 2013.
European Search Report of European Application No. 11769474.5 dated Sep. 5, 2013.
European Search Report of European Application No. 11796470.0 dated Jan. 5, 2016.
European Search Report of European Application No. 13760840.2, dated Feb. 4, 2016.
European Search Report of European Application No. 13721179.3 dated Mar. 23, 2016.
European Search Report for European Application No. 14749278.9 dated Jan. 13, 2017.
Extended European Search Report for European Application No. EP 12833859.7 dated Mar. 20, 2015.
Extended European Search Report for European Application No. EP 14787587.6 dated Jan. 2, 2017.
International Search Report and Written Opinion for International Application No. PCT/US2011/032181 dated Dec. 20, 2011.
International Search Report and Written Opinion for International Application No. PCT/US2011/040787 dated Feb. 27, 2012.
International Search Report and Written Opinion for International Application No. PCT/US2012/051804 dated Nov. 16, 2012.
International Search Report and Written Opinion for International Application No. PCT/US2013/037404 dated Jun. 21, 2013.
International Search Report and Written Opinion for International Application No. PCT/US2013/032705 dated Jul. 26, 2013.
International Search Report and Written Opinion for International Application No. PCT/US2013/050729 dated Sep. 25, 2013.
International Search Report and Written Opinion for International Application No. PCT/US2013/059640 dated Feb. 18, 2014.
International Search Report and Written Opinion for International Application No. PCT/US2014/015382 dated May 6, 2014.
International Search Report and Written Opinion for International Application No. PCT/US2014/035557 dated Aug. 27, 2014.
International Search Report and Written Opinion for International Application No. PCT/US2014/043930 dated Oct. 22, 2014.
International Search Report and Written Opinion for International Application No. PCT/US2014/046412 dated Oct. 27, 2014.
International Search Report and Written Opinion for International Application No. PCT/US2014/064088 dated Jan. 30, 2015.
International Search Report and Written Opinion for International Application No. PCT/US2015/010595 dated Apr. 15, 2015.
International Search Report and Written Opinion for International Application No. PCT/US2015/019755 dated May 4, 2015.
International Search Report and Written Opinion for International Application No. PCT/US2015/030009 dated Jul. 30, 2015.
International Search Report and Written Opinion for International Application No. PCT/US2015/039125 dated Sep. 30, 2015.
International Search Report and Written Opinion for International Application No. PCT/US2015/053200 dated Dec. 28, 2015.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/038233 dated Sep. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/044586 dated Oct. 21, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
International Search Report and Written Opinion for International Application No. PCT/US2017/015197 dated Apr. 3, 2017.
International Search Report and Written Opinion for International Application No. PCT/US2017/015450 dated Apr. 10, 2017.
International Search Report and Written Opinion for International Application No. PCT/US2016/047217 dated Apr. 11, 2017.
International Search Report and Written Opinion for International Application No. PCT/US2016/048243 dated Apr. 20, 2017.
International Search Report and Written Opinion for International Application No. PCT/US2017/017788 dated May 8, 2017.
International Search Report and Written Opinion for International Application No. PCT/US2017/030903 dated Jul. 19, 2017.

(56) References Cited

OTHER PUBLICATIONS

International Search Report and Written Opinion for International Application No. PCT/US2017/025108 dated Jul. 20, 2017.
International Search Report and Written Opinion for International Application No. PCT/US2017/031425 dated Aug. 30, 2017.
Sony New Release: <http://www.sony.net/SonyInfo/News/Press/201010/10-137E/index.html>.
International Search Report and Written Opinion for International Application No. PCT/US2017/031425 dated Oct. 23, 2017.
European Search Report of European Application No. 12825592.4 dated Apr. 28, 2015, 7 pages.
European Search Report of European Application No. 15847217.5 dated Oct. 15, 2018, 8 pages.
Extended European Search Report for EP Patent Application No. 19738317.7 dated Apr. 6, 2021, 6 pages.
Extended European Search Report received for European Patent Application No. 19764743.1 dated Dec. 3, 2021, 7 pages.
International Search Report and Written Opinion for International Application No. PCT/US18/63698, dated May 27, 2019, 14 pages.
International Search Report and Written Opinion for International Application No. PCT/US18/65839, dated May 16, 2019, 11 pages.
International Search Report and Written Opinion for International Application No. PCT/US19/12950, dated May 24, 2019, 13 pages.
International Search Report and Written Opinion for International Application No. PCT/US19/21492, dated Jun. 25, 2019, 16 pages.
International Search Report and Written Opinion for International Application No. PCT/US2017/057485, dated Jan. 4, 2018, 9 pages.
International Search Report and Written Opinion for International Application No. PCT/US2018/026617, dated Jul. 4, 2018, 11 pages.
International Search Report and Written Opinion for International Application No. PCT/US2018/31267, dated Aug. 1, 2018, 7 pages.
Ding et al., "Cell Separation Using Tilted-angle Standing Surface Acoustic Waves", PNAS Early Edition, 2014, 6 pages.
Ensminger et al., "Ultrasonics Fundamentals", Technologies, and Applications, 2011, 4 pages.
Evander et al., "Acoustofluidics 20: Applications in acoustic trapping", Lab on a Chip, vol. 12, Oct. 2012, pp. 4667-4676.
Gallego-Juarez et al., "Piezoelectric ceramics and ultrasonic transducers", Journal of Physics E: Scientific Instruments, 1989, pp. 804-816.
Ganguly et al., "Essential Physics for Radiology and Imaging", Academic Publishers, Jan. 2016, 3 pages.
Gorenflo et al., "Characterization and optimization of acoustic filter performance by experimental design methodology", Biotechnology Bioengineering, vol. 90, Issue 6., 2005, pp. 746-753.
Gor'kov L.P., "On the Forces Acting on a Small Particle in an Acoustical Field in an Ideal Fluid", Soviet Physics Doklady, vol. 6, Mar. 1962, pp. 773-775.
Greenhall et al., "Dynamic behavior of microscale particles controlled by standing bulk acoustic waves", Applied Physics Letters. vol. 105, 144105, 2014, 5 pages.
Jin Zuwei, "Expanded Bed Absorption-Challenges and Advances in Column and Process Design", Pharmaceutical Engineering, vol. 35 No. 1, Jan./Feb. 2015, 12 pages.
Lenshof et al., "Acoustofluidics 5: Building microfluidic acoustic resonators", Lab Chip, 12, 2012, pp. 684-695.
Mock et al., "Abstract: 2043 Automated Lentiviral Transduction of T Cells with Cars Using the Clinimacs Prodigy", ASH 57th Annual Meeting and Exposition, vol. 126, No. 23, 2015, 6 pages.
National Science Foundation,,"Catalyzing Commercialization: putting sound to work for challenQinQ separations", CEP, Sep. 2015, p. 14.
Nienow et al., "A potentially scalable method for the harvesting of hMSCs from microcarriers", Biochemical Engineering Journal, vol. 85, Apr. 15, 2014, pp. 79-88.
Shitizu et al., "A Tutorial Review on Bioprocessing Systems Engineering", 1996, pp. 915-941.
Woodside et al., "Acoustic force distribution in resonators for ultrasonic particle separation", vol. 44 Issue 9, Biotechnology Laboratory and Dept of Chemical and Bio-Resource Engineering, University of British Columbia, Sep. 1998, pp. 1976-1984.
Zhanqiu et al., "Culture Conditions and Types of Growth Media for Mammalian Cells (whole document)", InTechOpen, Biomedical Tissue Culture, 2012, 27 pages.
Lilliehorn et al., "Trapping of microparticles in the near field of an ultrasonic transducer", Ultrasonics, vol. 43, 2005, pp. 293-303.

\* cited by examiner

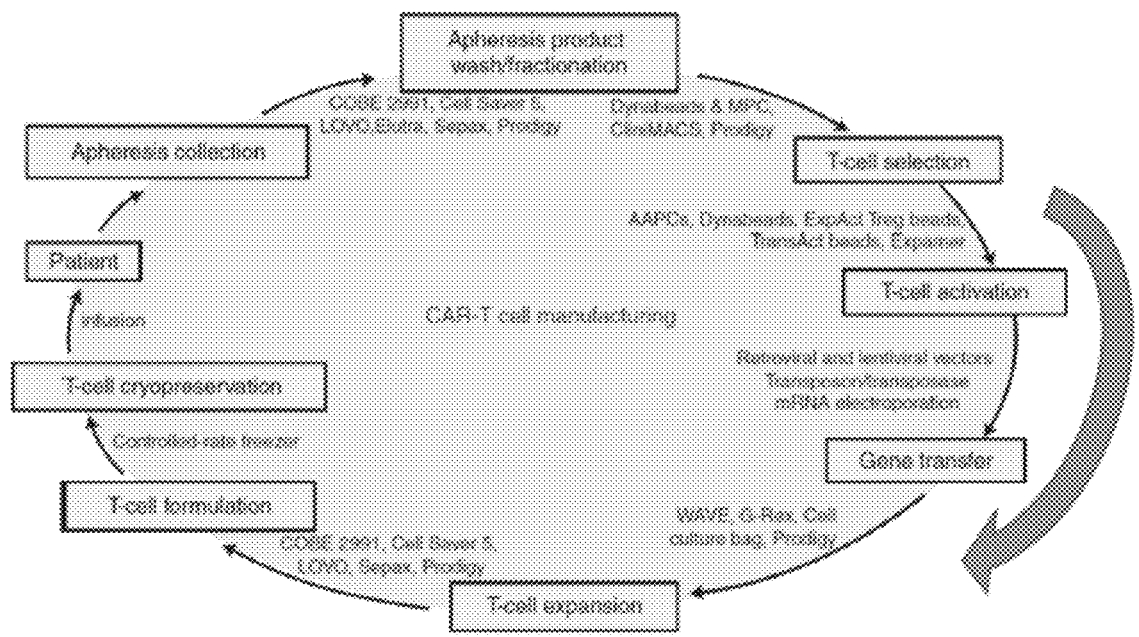
Fig. 1    100
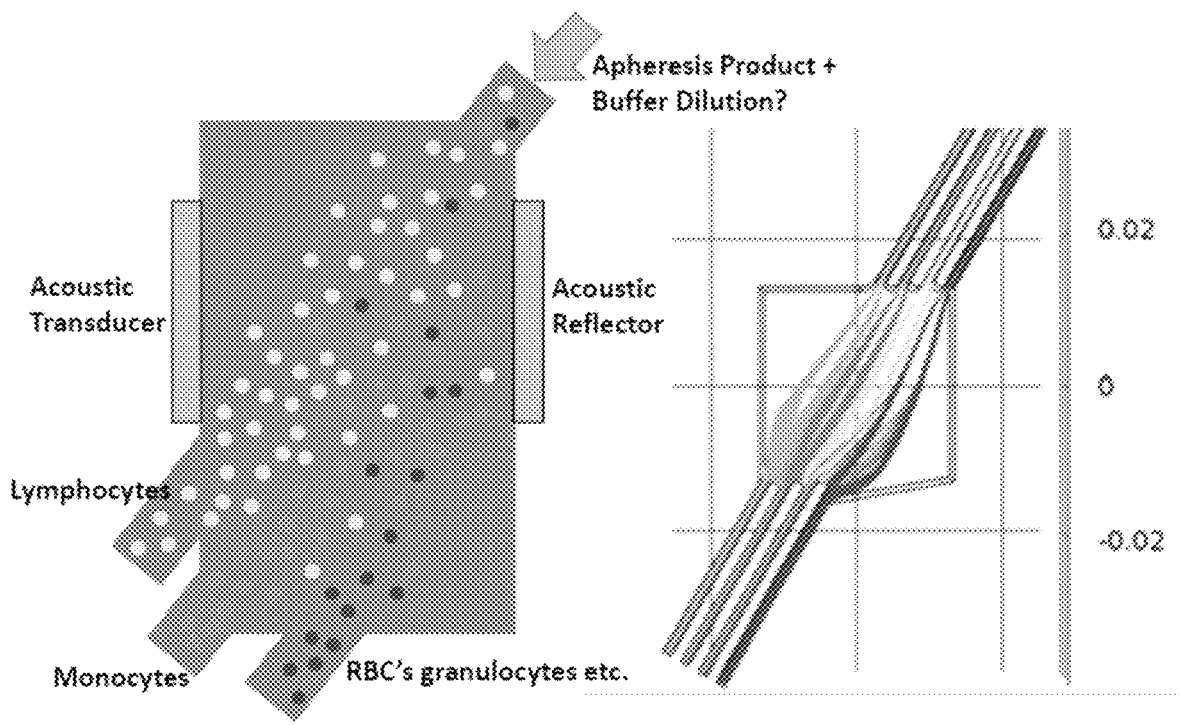
Fig. 2

CELL THERAPY PROCESSES UTILIZING ACOUSTOPHORESIS

CROSS-REFERENCE TO RELATED APPLICATIONS

This application is a continuation-in-part of U.S. patent application Ser. No. 15/788,784, filed on Oct. 19, 2017, which claims the benefit of U.S. Provisional Patent Application Ser. No. 62/410,312, filed on Oct. 19, 2016. This application also claims the benefit of U.S. Provisional Patent Application Ser. No. 62/468,895, filed on Mar. 8, 2017. The entire disclosures of these applications are hereby fully incorporated herein by reference.

BACKGROUND

Cell therapy is an immunology based therapy for treating a patient using cellular material. Current processes for implementing cell therapy treatments are associated with very high costs, on the order of $500,000-$1.5 million. A number of processes are used to produce the therapeutic product, with each process tending to be independent, open or nonsterile, and implemented by a highly skilled person or persons that often hold PhDs.

BRIEF SUMMARY

Cell therapy is a therapy that uses cellular material to treat a patient. Such a therapy sometimes involves obtaining cells, which may be provided by the patient, modifying the cells for therapeutic purposes, and introducing the cells into the patient. The production process for obtaining a final product that is introduced to the patient involves a number of steps or processes for handling and/or manipulating the cellular material. The present disclosure discusses a number of such processes that are implemented using acoustics to separate and/or retain and/or filter materials.

In some examples, a system is provided that is a closed and modular fluidic system composed of acoustic elements and cell processing reagents for a cellular manufacturing process on the scale of 30 to 150 billion cells and 750 mL to 5 L.

In some examples, the process steps include mononuclear cell (MNC) isolation from apheresis products, isolation of T-cells (CD3+, CD3+CD4+ and CD3+CD8+) from apheresis products, removal of T-cell receptor positive cells (TCR+ cells) post cell expansion, as well as several wash and volume change steps.

Implementations may include scale-dependent and/or scale-independent applications, or combinations thereof. Example implementations may control the cellular manufacturing process starting and final cell population and/or automate these process steps.

The various example processes may include one or more of the following, which may be independent or integrated or combined in various combinations or sequences. It should be understood that any types of cellular material may be processed with the disclosed acoustic cellular processing systems and methods. The following examples include processes for T-cells, and one or more of the processes may be applied, independently or in various combinations, to other types of cells.

An apheresis product is obtained, which may include a number of particles or components including T-cells, red blood cells (RBCs), platelets and/or granulocytes. The various components are separated, for example, with an acoustic process that differentiates the particles based on size, density, compressibility and/or acoustic contrast factor. In another example, T-cells are separated from the apheresis product using an affinity selection process. The affinity selection process may implement selection based on markers, including CD3+, CD3+CD4+, CD3+CD8+, for example. Another separation example provides label-free selection of mononucleated cells (MNC) from the apheresis product.

An example process provides for activation of the T-cells using a nanobead process in which acoustics are used to retain or pass the activated T-cells. The activated T-cells may be genetically modified with a lentiviral transduction operation, which may be implemented with an acoustic process that traps and/or co-locates the T-cells and lentivirus. The T-cells may be washed and/or concentrated and/or washed, in any desired order or to produce any desired results for concentrate/wash operations, using one or more acoustic devices that can retain the T cells and concentrate them into a reduced volume. The T-cells may be subjected to electroporation. The T-cells population may be expanded, such as by culturing, using an acoustic device that maintains or recycles the T cells in a culture in which the culture media is exchanged. The expanded T-cell population may be washed and/or concentrated and/or washed using one or more acoustic devices that can retain the T cells and concentrate them into a reduced volume. The T-cell culture may be separated to remove TCR+ cells, which may be achieved through negative selection using an affinity process that retains the TCR+ cells using acoustics. The resulting TCR−−CAR+ cells can be recovered using an acoustic process that separates those cells from the host fluid. A fill and finish process can be implemented on the recovered T cells to prepare a dose representing the final product.

In some example systems, a cell volume of about 30 billion cells or less can be processed in a one liter process. In some example systems, a cell volume of about 150 billion cells or less can be processed in a five liter process. In these example systems, the affinity selection of CD3+ T cells from apheresis products is Ficoll-free. In addition, or alternatively, the affinity selection of CD3+, CD3+CD4+ and/or CD3+CD8+, or any other type of marker selection desired, is Ficoll-free.

In some example systems, a concentrate-wash process and affinity selection process is integrated in a single device. The device can be configured to be used in a one or five liter process, or in any process scale desired.

In some example systems, the acoustic separation process for separating the apheresis components is implemented using an acoustic angled wave device. The acoustic angled wave device permits fractionation of different sized particles at different angles with an acoustic wave applied at an angle to a flow direction.

Concentrating therapeutic cells and transferring them from one solution into another (usually referred to as washing) is discussed herein. In particular, therapeutic cells may originally be suspended in a growth serum or in preservative materials like dimethyl sulfoxide (DMSO). Separating the cells from these fluids so the cells can be further processed is important in the overall therapeutic process of using such cellular materials. In one example, the cells are typically recovered from a bioreactor, concentrated, and transferred from culture media into an electroporation buffer prior to transduction, such as in manufacturing CAR-T cells. After expansion of cells at the final manufacturing step, they are concentrated and transferred into an appropriate solvent depending on the desired application.

Therapeutic cells are stored in specialized media to prolong the viability of these cells either through refrigeration and or freezing processes. Such specialized media may not be compatible when the therapeutic cells are introduced into a patient. It may thus be helpful to both wash and concentrate the therapeutic cells in a buffer or wash media that is biocompatible with both the therapeutic cells and with the patient. The washing step may be repeated a number of times. For example, the specialized media (which can be pyrogenic or otherwise harmful) may be fully removed with multiple wash steps, and the cells may be suspended in a new buffer or wash solution.

Separation of biomaterials can be accomplished by functionalized material distributed in a fluid chamber. The functionalized material bind the specific target materials such as recombinant proteins and monoclonal antibodies or cells. The functionalized material, which may take a form of microcarriers that are coated with an affinity protein, is trapped by nodes and/or anti-nodes of an acoustic standing wave. In this approach, the functionalized material is trapped without contact (for example, using mechanical channels, conduits, tweezers, etc.).

The present disclosure provides methods and systems for replacing or augmenting conventional centrifugation and physical filtration processes along with the multiple washing steps with a simpler, lower cost, and more friendly process for particles such as therapeutic cells. The methods/processes can be performed in a sterile/closed environment and in a continuous form.

Disclosed herein are methods of washing particles, which comprise feeding an initial mixture of a first media and the particles through a flow chamber of an acoustophoretic device. For example, the first media may contain preservatives such as dimethyl sulfoxide (DMSO) which are undesirable for future applications/uses of the particles, such as cells. The acoustophoretic device also comprises at least one ultrasonic transducer that includes a piezoelectric material that is configured to be driven to create a multi-dimensional acoustic standing wave in the flow chamber. The at least one ultrasonic transducer is driven to create a multi-dimensional acoustic standing wave in the flow chamber, such that at least a portion of the particles are trapped in the multi-dimensional acoustic standing wave. The trapped particles are subsequently mixed with a second media to wash the trapped particles (e.g. remove the first media from the particles).

In some embodiments, the initial mixture is run through the flow chamber to obtain an intermediate mixture of the particles in a reduced volume of the first media. The intermediate mixture is then collected, and mixed together with the second media to form a secondary mixture. The secondary mixture is then fed through the flow chamber to obtain a final mixture of particles in a reduced volume of the second media.

In other embodiments, the second media is fed into the flow chamber after the initial mixture is fed through the flow chamber. Here, the second media displaces the first media, or gradually replaces the first media. The second media can be a biocompatible wash or a buffer solution.

In still other embodiments, the acoustophoretic device further comprises a collector located below the at least one ultrasonic transducer so that as the trapped particles form clusters and grow to a critical size and subsequently fall out of the multi-dimensional acoustic standing wave, the clusters fall into the collector. The collector leads to a collection container that contains the second media, mixing the clusters of particles together with the second media.

The particles may be cells. The cells may be Chinese hamster ovary (CHO) cells, NSO hybridoma cells, baby hamster kidney (BHK) cells, human cells, regulatory T-cells, Jurkat T-cells, CAR-T cells, B cells, or NK cells, peripheral blood mononuclear cells (PBMCs), algae, plant cells, bacteria, or viruses. The cells may be attached to microcarriers.

Sometimes, the piezoelectric material of the at least one ultrasonic transducer is in the form of a piezoelectric array formed from a plurality of piezoelectric elements. Each piezoelectric element can be physically separated from surrounding piezoelectric elements by a potting material. The piezoelectric array can be present on a single crystal, with one or more channels separating the piezoelectric elements from each other. Each piezoelectric element can be individually connected to its own pair of electrodes. The piezoelectric elements can be operated in phase with each other, or operated out of phase with each other. The acoustophoretic device may further comprise a cooling unit for cooling the at least one ultrasonic transducer.

Also disclosed herein are acoustophoretic systems, comprising an acoustophoretic device with a port that may operate as a wash inlet, a concentrate outlet and/or a wash outlet. The acoustophoretic device may include one or more ultrasonic transducers including a piezoelectric material. The piezoelectric material can be excited to form a standing wave on its surface, which can generate a multi-dimensional acoustic standing wave in an adjacent fluid.

BRIEF DESCRIPTION OF THE DRAWINGS

The following is a brief description of the drawings, which are presented for the purposes of illustrating the example embodiments disclosed herein and not for the purposes of limiting the same.

FIG. 1 is a block diagram of a cell therapy production process.

FIG. 2 is a diagram of an acoustic angled wave process.

FIG. 8 is a conventional single-piece monolithic piezoelectric material used in an ultrasonic transducer.

DETAILED DESCRIPTION

Figure 3:
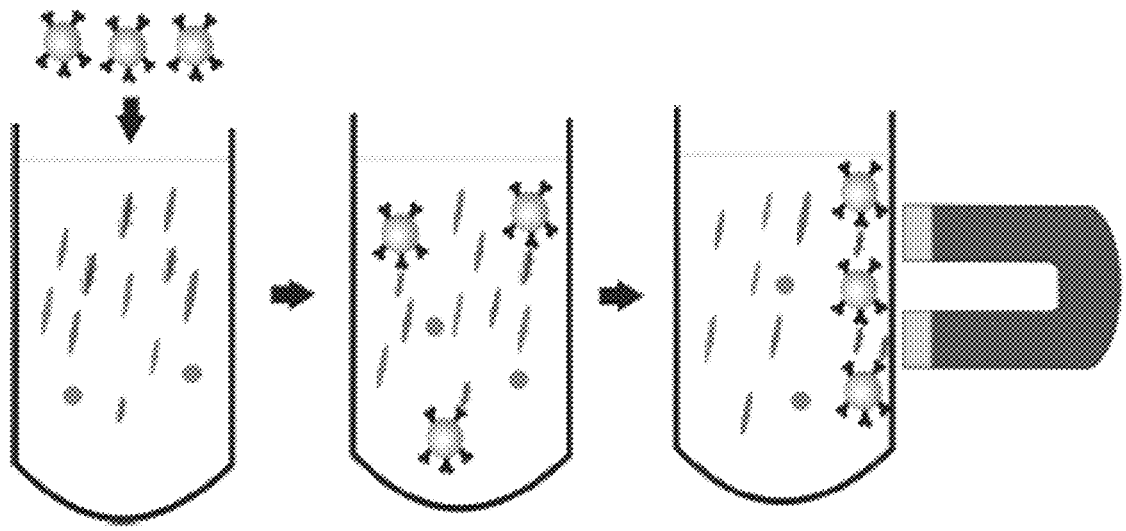
FIG. 3 is a diagram illustrating a magnetically activated affinity process.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing compositions or processes as "consisting of" and "consisting essentially of" the enumerated components/steps, which allows the presence of only the named components/steps, along with any impurities that might result therefrom, and excludes other components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4."

It should be noted that many of the terms used herein are relative terms. For example, the terms "upper" and "lower" are relative to each other in location, e.g. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, e.g. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, e.g. ground level. The terms "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value of at least 1 and less than 10.

Cell Therapy Processes

Cell therapy is a therapy that uses cellular material to treat a patient. Such a therapy sometimes involves obtaining cells, which may be provided by the patient, modifying the cells for therapeutic purposes, and introducing the cells into the patient. The production process for obtaining a final product that is introduced to the patient involves a number of steps or processes for handling and/or manipulating the cellular material. The present disclosure discusses a number of such processes that are implemented using acoustics to separate and/or retain and/or filter materials.

In some examples, a system is provided that is a closed and modular fluidic system composed of acoustic elements and cell processing reagents for a cellular manufacturing process on the scale of 30 to 150 billion cells and 750 mL to 5 L.

In some examples, the process steps include mononuclear cell (MNC) isolation from apheresis products, isolation of T-cells (CD3+, CD3+CD4+ and CD3+CD8+) from apheresis products, removal of T-cell receptor positive cells (TCR+ cells) post cell expansion, as well as several wash and volume change steps.

Implementations may include scale-dependent and/or scale-independent applications, or combinations thereof. Example implementations may control the cellular manufacturing process starting and final cell population and/or automate these process steps.

The various example processes may include one or more of the following, which may be independent or integrated or combined in various combinations or sequences. It should be understood that any types of cellular material may be processed with the disclosed acoustic cellular processing systems and methods. The following examples include processes for T-cells, and one or more of the processes may be applied, independently or in various combinations, to other types of cells.

Referring to FIG. 1, a block diagram 100 illustrates various steps in a cell production process. The process is directed to T cells, however, any type of cellular material can be processed with the acoustic devices described herein. The various steps illustrated are apheresis collection, apheresis product wash/fractionation, T-cell selection, T-cell activation, gene transfer, T-cell expansion, T-cell formulation and T-cell cryopreservation. In accordance with the present disclosure, acoustic processing can be applied to some or all of these steps, some of which may be combined or integrated within a single acoustic device.

As illustrated in diagram 100, an apheresis product is obtained, which may include a number of particles or components including T-cells, red blood cells (RBCs), platelets and/or granulocytes. The various components are separated, for example, with an acoustic process that differentiates the particles based on size, density, compressibility and/or acoustic contrast factor. In another example, T-cells are separated from the apheresis product using an affinity selection process. The affinity selection process may implement selection based on markers, including CD3+, CD3+CD4+, CD3+CD8+, for example. Another separation example provides label-free selection of mononucleated cells (MNC) from the apheresis product.

Diagram 100 illustrates activation of the T-cells using a nanobead process in which acoustics are used to retain or pass the activated T-cells. The activated T-cells may be subjected to a gene transfer process, which may involve a lentiviral transduction operation, which may be implemented with an acoustic process that traps and/or co-locates the T-cells and lentivirus. The T-cells may be washed and/or concentrated and/or washed, in any desired order or to produce any desired results for concentrate/wash operations, using one or more acoustic devices that can retain the T cells and concentrate them into a reduced volume. The T-cells population may be expanded, such as by culturing, using an acoustic device that maintains or recycles the T cells in a culture in which the culture media is exchanged. The expanded T-cell population may be washed and/or concentrated and/or washed using one or more acoustic devices that can retain the T cells and concentrate them into a reduced volume. The T-cell culture may be separated to remove TCR+ cells, which may be achieved through negative selection using an affinity process that retains the TCR+ cells using acoustics. The resulting TCR--CAR+ cells can be recovered using an acoustic process that separates those cells from the host fluid. A fill and finish process can be implemented on the recovered T cells to prepare a dose representing the final product.

Acoustic Angled Wave Separation

RBC depletion and other fractionation processes may be implemented using angled wave technology. The fractionation of RBC, granulocyte, platelet and MNC using the angled wave device is discussed below. FIG. 2 illustrates an acoustic transducer that generates a bulk acoustic wave within a fluid flow with a mean direction flow that is angled relative to the acoustic wave. The angled acoustic wave can cause particles within the fluid to deflect at different angles that depend upon various characteristics of the particles. Thus, bulk acoustic standing waves angled relative to a direction of flow through a device can be used to deflect, collect, differentiate, or fractionate particles or cells from a fluid flowing through the device. FIG. 2 illustrates generation of angled acoustic standing waves due to the acoustic waves being reflected with the acoustic reflector. It should be understood that any type of acoustic wave may be used, including traveling waves, which may be implemented without an acoustic reflector, or maybe implemented with an acoustic absorber. The illustrated acoustic standing wave can be used to separate or fractionate particles in the fluid by, for example, size, density, speed of sound, and/or shape. The angled acoustic standing wave can be a three-dimensional acoustic standing wave. The acoustic standing wave may also be a planar wave where the piezoelectric material of the acoustic transducer is excited in a piston fashion, or the acoustic standing waves may be a combination of the planar acoustic standing waves and the multidimensional acoustic standing waves. The deflection of the particles by the standing wave can also be controlled or amplified by the strength of the acoustic field, the angle of the acoustic field, the properties of the fluid, the dimensionality or mode of the standing wave, the frequency of the standing wave, the acoustic chamber shape, and the mixture flow velocity.

When acoustic standing waves propagate in liquids, the fast oscillations may generate a non-oscillating force on particles suspended in the liquid or on an interface between liquids. This force is known as the acoustic radiation force. The force originates from the non-linearity of the propagating wave. As a result of the non-linearity, the wave is distorted as it propagates and the time-averages are nonzero. By serial expansion (according to perturbation theory), the first non-zero term will be the second-order term, which accounts for the acoustic radiation force. The acoustic radiation force on a particle, or a cell, in a fluid suspension is a function of the difference in radiation pressure on either side of the particle or cell. The physical description of the radiation force is a superposition of the incident wave and a scattered wave, in addition to the effect of the non-rigid particle oscillating with a different speed compared to the surrounding medium thereby radiating a wave.

As illustrated in FIG. 2, an apheresis product is fractionated into lymphocytes, monocytes and RBCs, granulocytes and other particles. This process can be used to isolate T cells in the apheresis product.

Affinity Separation

The affinity separation of biological materials, such as proteins or cells, is accomplished in some examples through the use of a ligand that is covalently bonded to a structure, such as a microbead. The ligand interacts with the protein or cell such that the protein or cell is bound to the ligand on the microbead.

A ligand is a substance that forms a complex with the biomolecules. With protein-ligand binding, the ligand is usually a molecule which produces a signal by binding to a site on a target protein the binding typically results in a change of confirmation of target protein. The ligand can be a small molecule, ion, or protein which binds to the protein material. The relationship between ligand and binding partner is a function of charge, hydrophobicity, and molecular structure. Binding occurs by intermolecular forces such as ionic bonds, hydrogen bonds and van der Waals forces. The Association of docking is actually reversible through disassociation. Measurably irreversible covalent bonds between the ligand and target molecule is a typical in biological systems.

A ligand that can bind to a receptor, alter the function of the receptor, and trigger a physiological response is called an agonist for the receptor. Agonist binding to receptor can be characterized both in terms of how much physiological response can be triggered and in terms of the concentration of the agonist that is required to produce the physiological response. High affinity ligand binding implies that the relatively low concentration of the ligand is adequate to maximally occupy a ligand—binding site and trigger a physiological response. The lower the Ki level is, the more likely there will be a chemical reaction between the pending and the receptive antigen. Low—affinity binding (high Ki level) implies that a relatively high concentration of the ligand is required before the binding site is maximally occupy and the maximum physiological response to the ligand is achieved. Bivalent ligands consist of two connected molecules as ligands, and are used in scientific research to detect receptor timers and to investigate the properties.

The T cell receptor, or TCR, is a molecule found on the surface of T cells or T lymphocytes, that is responsible for recognizing fragments of antigen as peptides bound to major histocompatibility complex (MHC) molecules. The binding between TCR and antigen peptides is of relatively low affinity and is degenerative.

Referring to FIG. 3, paramagnetic beads, such as iron or ferro-magnetic beads sold under the name Dynabeads, have been used to achieve affinity extraction. The magnetic beads, coated with a functionalized material, bind to biological targets in complex mixtures to permit the target material to be separated out of the complex mixture using a magnetic field. The beads carry molecules for affine binding various targets with high specificity. The beads are injected into the complex mixture and incubated to bind the targets. The beads are extracted by a magnet together with the targets attached to the beads.

Micro sized beads are available, such as, e.g., Dynabeads, which are on the order of 4.5 µm in size. Nano sized beads may be used, such as, e.g., Myltenyi, which are on the order of 50 nm in size. Some of the affine molecules that may be used include antibodies, aptamers, oligonucleotides and receptors, among others. The targets for the affinity binding may include biomolecules, cells, exosomes, drugs, etc.

Figure 4:
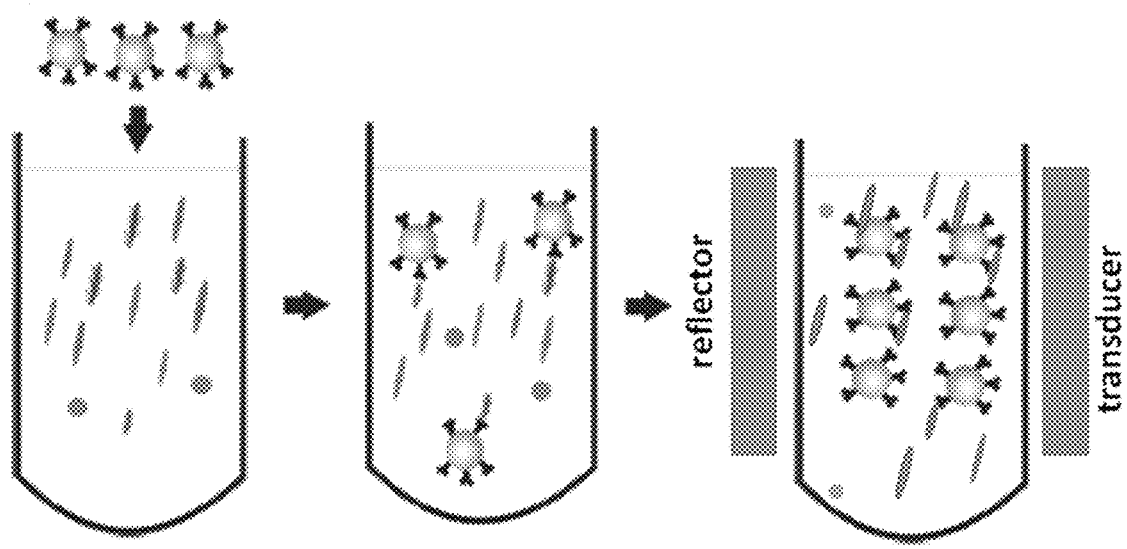
FIG. 4 is a diagram illustrating an acoustically activated affinity process.

Referring to FIG. 4, beads with high acoustic contrast and affinity chemistry are illustrated. These acoustic beads can be used in exactly the same way as magnetic beads with regard to having functionalized material coatings or composition for affinity binding. The acoustic beads are designed to be extracted from a complex mixture or fluid with an acoustic field. The acoustic beads can be directly used in all the applications developed in cell manufacturing, biochemistry, diagnostics, sensors, etc. that use magnetic beads.

The acoustic beads can use the same surface and affinity chemistry as is used with magnetic beads. This ease of substitution of acoustic beads for magnetic beads has many advantages, including simplifying approval for applications, as well as simplifying the applications.

The acoustic beads can be made biocompatible. Such beads can be produced in different sizes, which permits continuous separation based on size in a size differentiating acoustic field, such as may be provided with an angled-field fractionation technology. The acoustic beads can be combined with an enclosed acoustics-based system, leading to a continuous end-to-end cycle for therapeutic cell manufacturing. This functionality provides an alternative to magnetic bead extraction, while preserving use of currently existing affinity chemistry, which can be directly transferred to the acoustic beads. The acoustic beads may be a consumable product in the separation operation.

In an example, a proof of concept trial was made using the published Memorial Sloan Kettering Cancer Center (MSKCC) protocol for extraction of CD3+ T cells from patient's blood. In the trial, paramagnetic beads were used, and the magnetic field is replaced with an acoustic field. The process of extracting CD3+ T cells from patient's blood is an integral part of manufacturing CAR (chimeric antigen receptor) T cells. Current processes are based on commercially available CD3 Dynabeads. In the trial, efforts were made to minimize the protocol differences, including performing the experiments in culture broth, rather than blood. The difference is considered reduced since several steps in CAR T cell manufacturing work from broth. The solvent density was increased to make T cells "acoustically invisible," or not as susceptible to an acoustic field. The small size of the Dynabeads may provide an acoustic contrast that is similar to the cells, thus making separation tolerances smaller. The trial employed Jurkat CD3+ and CD3− T cell lines as models. The CD3− cells were employed as a control for non-specific trapping.

The cell suspensions were incubated with CD3 Dynabeads, which bound CD3+ cells. The mixture was passed through the acoustic system, which trapped the magnetic beads (with or without cells). The collected cells were successfully grown in culture. They cultured cells were examined with overlap of bright field images with fluorescence images. The beads were black with slight reddish autofluorescence. The live cells were fluorescent red. The bead diameter is 4.5 microns. CD3+ T-cell complexes with beads were observed, which demonstrates the efficiency of the technique. No CD3− T-cells were extracted in this example, which demonstrates the specificity and selectivity of the technique.

Figure 5:
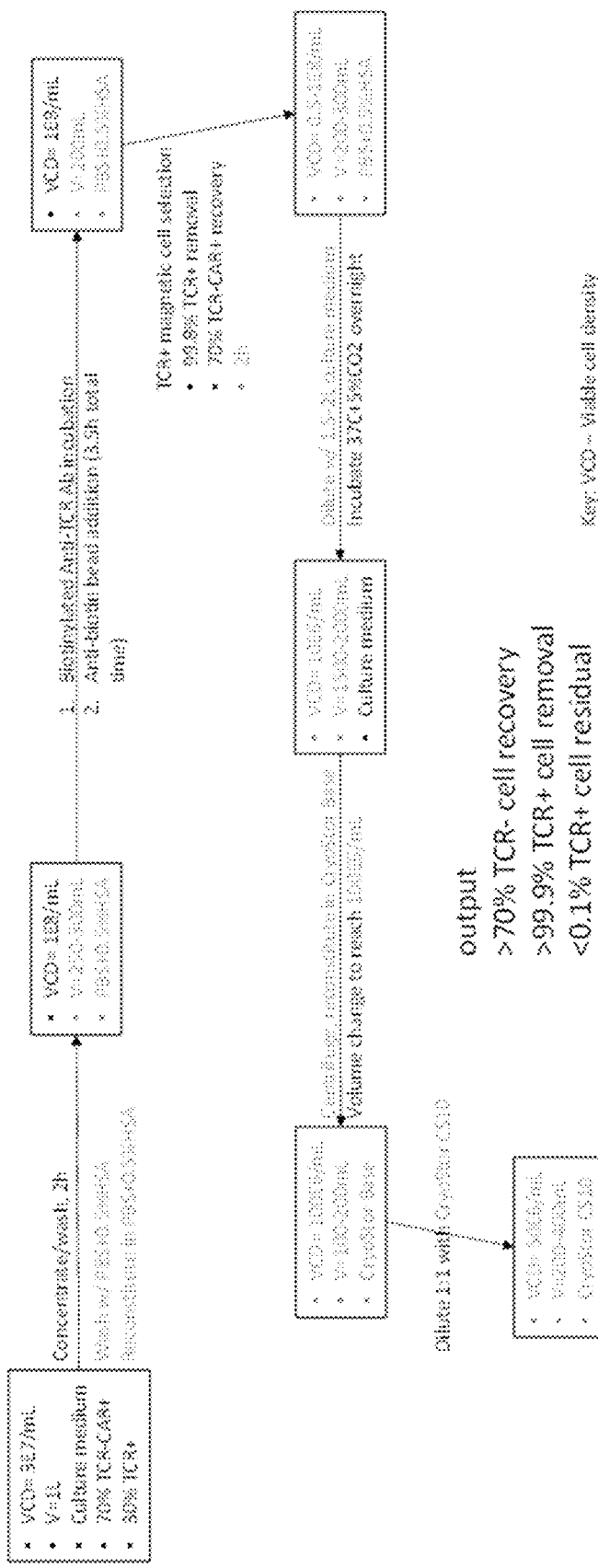
FIG. 5 is a flowchart illustrating a process for depletion of TCR+ cells.

Referring to FIG. 5, a process for affinity selection and removal of TCR+ cells is illustrated. The process steps include a concentrate/wash step, followed by incubation with biotinylated anti-TCR Ab beads. The beads are used to select and remove TCR+ cells through a magnetic process, followed by a culturing and centrifuge process. In accordance with the present disclosure, acoustically sensitive beads are used instead of magnetic selection beads. The acoustic beads may have the same or similar surface chemistry as the magnetic beads. The acoustic beads may be used to select and remove the TCR+ cells has discussed herein.

In an example, a trial with acoustic beads was conducted. In this trial, agarose beads were used as the acoustic beads. These beads are available off-shelf from several manufacturers, and are not paramagnetic or have little to none iron or ferro magnetic content. Some agarose beads have surface modifications that simplify antibody attachment. They are also composed of biocompatible material, which can be important for therapeutic solutions. For example, ABT-Beads, which are relatively inexpensive, heterogeneous (20-150 μm), off-shelf beads, which are available with streptavidin and biotin conjugates can be used. CellMosaic agarose beads, which tend to be relatively expensive, homogeneous (20-40 μm) can be configured with any modification by order.

The acoustic beads can be trapped in an acoustic field, such as a multi-dimensional acoustic standing wave. Proof-of-concept and validation of performance has been shown using acoustic affinity beads in an acoustic system. The disclosed methods and systems permit the use of off-shelf reagents, and currently available acoustic systems. The affinities can target any type of desired T cells or markers including TCR+, CD3+, CD4+, CD8+. The acoustic beads can have a high, neutral or low contrast factor, which can affect how the beads respond to an acoustic field, for example being urged toward an acoustic node or antinode, or passing through the field.

The beads may be composed of various materials and combinations, which permits development of optimal chemistry with acoustic performance and biocompatibility. The beads may be processed for isolation, sorting or any other function useful in a separation process. When used with a tuned acoustic system, the performance of specifically designed acoustic beads can match or exceed that of paramagnetic beads.

Existing chemistries may be used with the acoustic beads, and in conjunction with specifications of size and structure homogeneity to achieve desired results for acoustic and for isolation performance. The beads may be composed of composite constructs to advance acoustic efficiency. The acoustic system provides flexibility to manage small sizes, with heat management, and the use of fluidics to obtain results that are not possible with paramagnetic beads alone. The biocompatibility and/or biodegradability of the acoustic beads and simplified processing permits integration with existing hardware for CAR T cell manufacturing. The affinity acoustic beads can be used in a number of environments, including model environments such as, e.g., animal blood spiked with target cells and murine spleen extracts. The acoustic beads may thus be used in collaboration with existing systems, and may be designed and manufactured for target applications. The beads may be provided with a core that is acoustically active or neutral, and the bead themselves may be configured for high, neutral or low acoustic contrast. The size of the beads may be configured for separation and affinity in combination, for example a certain sized bead may include functionalized material to target a certain biomaterial, while another sized bead, may be functionalized to target another biomaterial, each of which can be separated simultaneously and continuously in a closed or flowing system. The beads can be designed to be of a homogeneous size distribution within a narrow or relatively broad range. Various affinity chemistries may be used, including streptavidin-biotin complex and immunoglobulin or aptamer. The beads may be designed for ease of manufacturability and/or for shelf-life. The beads may be used with approved chemistries, so that they may readily be integrated into known systems that use approved chemistries.

Affinity negative selection of TCR+ cells with a volume of 1 L and 30 billion cells was specified in an example trial. In a parallel trial, affinity negative selection of TCR+ cells with a volume of 5 L and 150 billion cells was specified. Table 1 summarizes the results for the trials.

TABLE 1

| Item | Baseline | Preferred |
| --- | --- | --- |
| Initial volume (flexible if FDS owns previous stage of the process) | 1 L (5 L) | |
| Final volume | 100-200 mL (500-1000 mL) | |
| Total viable cells | 30 B (150 B) | |
| Viable TCR$^-$CAR$^+$ cell recovery | 70% | >70% |
| TCR$^+$ cell removal efficiency | 99.9% | >99.9% |

Affinity selection of CD3+ cells from an apheresis product was specified in an example trial. Table 2 summarizes the results for the trial.

TABLE 2

| Item | Baseline | Preferred |
| --- | --- | --- |
| Initial volume | 300 mL | |
| Final volume | To be adjusted for activation | |
| Total viable cells | 15 B MNCs (correct if T-cells) | |
| Viable CD3$^+$ cell recovery | 80% | >80% |
| Purity | 95% CD3$^+$ | >95% |

Affinity selection of CD3+CD4+ and CD3+CD8+ cells from an apheresis product was specified in an example trial. Table 3 summarizes the results for the trial.

TABLE 3

| Item | Baseline | Preferred |
| --- | --- | --- |
| Initial volume | 300 mL | |
| Final volume | To be adjusted for activation | |
| Total viable cells | 15 B MNCs | |
| Viable CD3 + CD4+ and CD3 + CD8+ cell recovery | 80% | >80% |
| Purity | 95% CD3 + CD4+ and CD3 + CD8+ | >95% |

Label-free selection of mononucleated cells (MNC) from apheresis product was specified in an example trial. Table 4 summarizes the results for the trial.

TABLE 4

| Requirement | Baseline | Preferred |
| --- | --- | --- |
| Initial volume | 300 mL | |
| Final volume | To be adjusted for activation | |
| Total viable cells | 15 B MNCs (correct if T-cells) | |
| Viable MNC recovery | 80% | >80% |
| RBC, Platelets and Granulocyte removal efficiency | 99% | >99% |

Concentrate/Wash

The acoustophoretic technology of the present disclosure employs acoustic standing waves to concentrate, wash, and/or separate materials (such as particles or a secondary fluid) in a primary or host fluid. In particular, as shown in the upper left image (A) of FIG. 6, an ultrasonic transducer T creates an acoustic wave in the fluid, which interacts with a reflector R positioned across from the ultrasonic transducer to create an acoustic standing wave. Although a reflector R is illustrated in FIG. 6, another transducer may be used to reflect and/or generate acoustic energy to form the acoustic standing wave.

Figure 6:
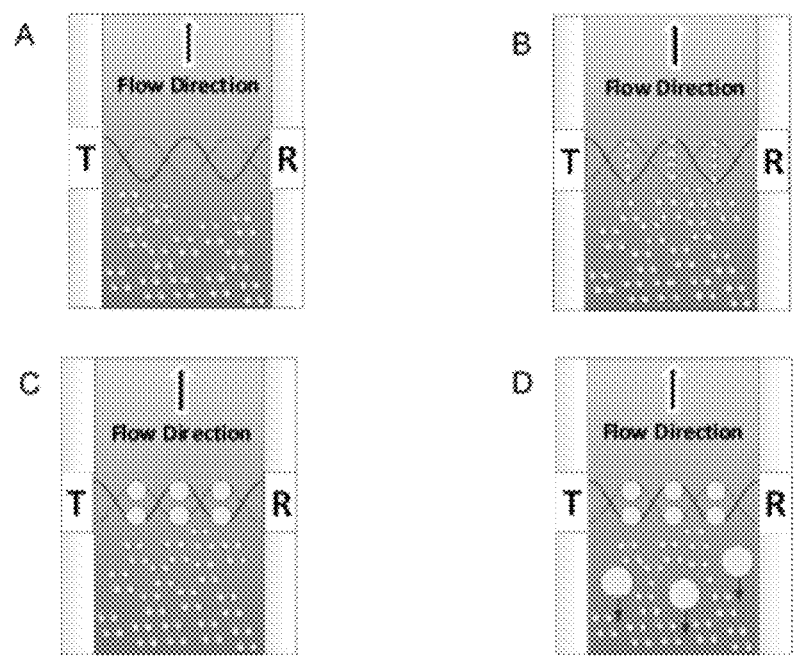
FIG. 6 is a set of diagrams illustrating an acoustic separation process.

As shown in the upper right image (B) of FIG. 6, as the host fluid and material entrained in the host fluid flows upwards through the acoustic standing wave, the acoustic standing wave(s) traps (retains or holds) the material (e.g., secondary phase materials, including fluids and/or particles). The scattering of the acoustic field off the material results in a three-dimensional acoustic radiation force, which acts as a three-dimensional trapping field.

The three-dimensional acoustic radiation force generated in conjunction with an ultrasonic standing wave is referred to in the present disclosure as a three-dimensional or multi-dimensional standing wave. The acoustic radiation force is proportional to the particle volume (e.g. the cube of the radius) of the material when the particle is small relative to the wavelength. The acoustic radiation force is proportional to frequency and the acoustic contrast factor. The acoustic radiation force scales with acoustic energy (e.g. the square of the acoustic pressure amplitude). For harmonic excitation, the sinusoidal spatial variation of the force drives the particles to the stable positions within the standing waves. When the acoustic radiation force exerted on the particles is stronger than the combined effect of fluid drag force and buoyancy and gravitational force, the particle can be trapped within the acoustic standing wave field, as shown in the upper right image (B) of FIG. 6.

As can be seen in the lower left image (C) of FIG. 6, this trapping results in coalescing, clumping, aggregating, agglomerating, and/or clustering of the trapped particles. Additionally, secondary inter-particle forces, such as Bjerkness forces, aid in particle agglomeration.

As the particles continue to coalesce, clump, aggregate, agglomerate, and/or cluster the particles can grow to a certain size at which gravitational forces on the particle cluster overcome the acoustic radiation force. At such size, the particle cluster can fall out of the acoustic standing wave, as shown in the lower right image (D) of FIG. 6.

Desirably, the ultrasonic transducer(s) generate a three-dimensional or multi-dimensional acoustic standing wave in the fluid that exerts a lateral force on the suspended particles to accompany the axial force so as to increase the particle trapping capabilities of the standing wave. A planar or one-dimensional acoustic standing wave may provide acoustic forces in the axial or wave propagation direction. The lateral force in planar or one-dimensional acoustic wave generation may be two orders of magnitude smaller than the axial force. The multi-dimensional acoustic standing wave may provide a lateral force that is significantly greater than that of the planar acoustic standing wave. For example, the lateral force may be of the same order of magnitude as the axial force in the multi-dimensional acoustic standing wave.

The acoustic standing waves of the present disclosure can be used to trap particles (e.g. therapeutic cells such as T cells, B cells, NK cells) suspended in a first media in the standing wave. The first media can then be replaced with a second media (e.g., a biocompatible wash or buffer solution). Put another way, the host fluid of the particles can be replaced. Prior to replacing the first media with the second media, acoustophoresis can be used to perform a diafiltration process, as shown in FIG. 7.

Figure 7:
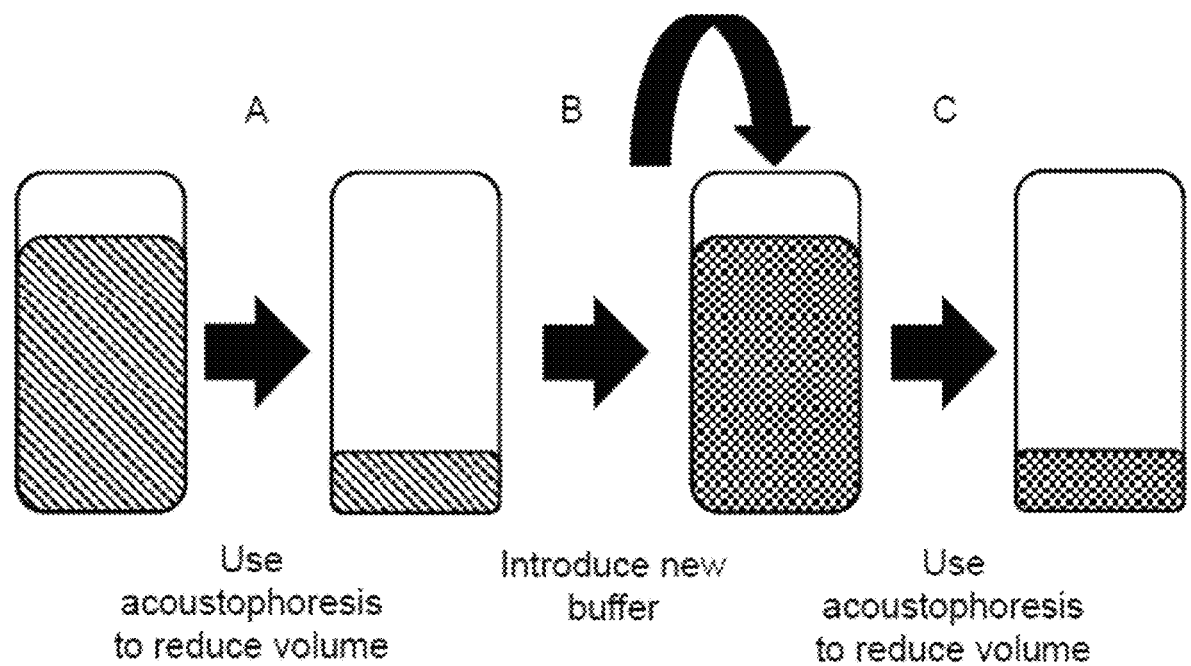
FIGS. 7 and 8 are a set of diagrams illustrating a concentrate-wash operation.

In FIG. 7, starting with an initial mixture that has a low cell density of, for example, less than $1\times10^6$ cells/mL, acoustophoresis can be used to reduce the volume of the initial mixture, for example by at least 10×, including 20× and up to 100× or more. The cell concentration may be increased by at least 10×, including 20× and up to 100× or more. This initial reduction process is the first volume reduction step (A). Next, the second media (e.g., a biocompatible wash or buffer solution) can be introduced to at least partially displace the first media, as indicated in step (B). Next, the new mixture of the cells and second media can be subjected to an acoustophoretic volume reduction step (C). This series of operations is referred to as a "diafiltration" process.

Figure 8:
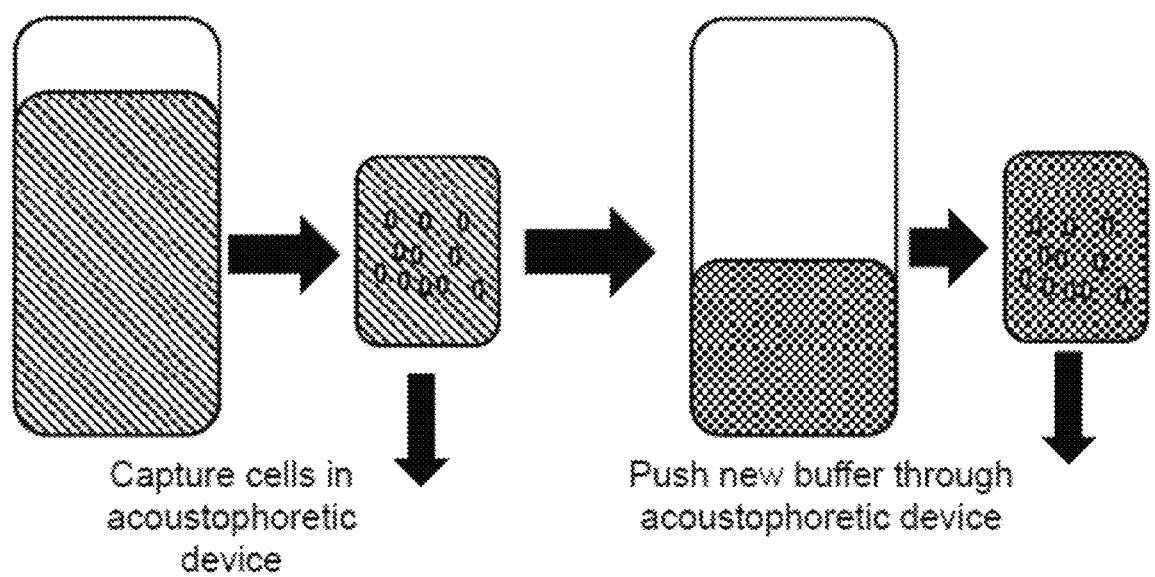

FIG. 8 illustrates a single-step, push-through process in which particles/cells are trapped in the acoustic standing wave and held in the acoustophoretic device. The second media (e.g., a biocompatible wash or buffer solution) is then flowed into the acoustophoretic device to effectively "wash out" the first media. With the push-through process, more than 90%, including up to 99% or more, of the first media can be removed from the particles/cells. The push-through process can be employed as a continuous, single-use process that uses less buffer solution and less time than the diafiltration process of FIG. 7.

The piezoelectric transducer(s) of the acoustophoretic devices and systems of the present disclosure can be single monolithic piezoelectric materials or can be made from an array of piezoelectric materials. The piezoelectric material can be a ceramic material, a crystal or a polycrystal, such as PZT-8 (lead zirconate titanate). The outer surface and the inner surface are relatively large in area, and the crystal is relatively thin (e.g. about 0.040 inches for a 2 MHz crystal).

Each piezoelectric element in the piezoelectric array of the present disclosure may have individual electrical attachments (e.g. electrodes), so that each piezoelectric element can be individually controlled for frequency and power. These elements can share a common ground electrode. This configuration allows for not only the generation of a multi-dimensional acoustic standing wave, but also improved control of the acoustic standing wave. In this way, it is possible to drive individual piezoelectric elements (or multiple, separate ultrasonic transducers) with arbitrary phasing and/or different or variable frequencies and/or in various out-of-phase modes.

The concentration efficiency of the acoustophoretic device was tested. First, a T-cell suspension having a cell density of $1\times10^6$ cells/mL was used. A feed volume of between about 500 and 1000 mL was used at a flow rate of 10-15 mL/minute. The device exhibited a concentration factor of between 10× and 20×, a 90% cell recovery, and a 77% washout efficiency (e.g., the amount of the first media that was displaced by the second media) over ten minutes of testing. A 10° C. temperature increase was observed.

The concentration efficiency of the acoustophoretic device was again tested with a higher cell density. A T-cell suspension having a cell density of 5×106 cells/mL was used. A feed volume of 1000 mL was used at a flow rate of 10-15 mL/minute. The device exhibited a concentration factor of better than 10×, a 90% cell recovery, and a 77% washout efficiency over one hour of testing. A 10° C. temperature increase was again observed.

During testing, it was also discovered that active cooling of the ultrasonic transducer led to greater throughput and efficiency and more power. As such, a cooling unit was developed for actively cooling the transducer. The cooling unit includes an independent flow path that is separate from the flow path through the device containing the fluid that is to be exposed to the multi-dimensional acoustic standing wave. A coolant inlet is adapted to permit the ingress of a cooling fluid into the cooling unit. A coolant outlet serves as the outlet through which the coolant and waste heat exit the cooling unit. Here, the coolant inlet is located below the coolant outlet, though this path can be varied as desired. The coolant that flows through the cooling unit can be any appropriate fluid. For example, the coolant can be water, air, alcohol, ethanol, ammonia, or some combination thereof. The coolant can, in certain embodiments, be a liquid, gas, or gel. The coolant can be an electrically non-conductive fluid to prevent electric short-circuits. The cooling unit can be used to cool the ultrasonic transducer, which can be particularly advantageously when the device is to be run continuously with repeated processing and recirculation for an extended period of time (e.g., perfusion). The cooling unit can also be used to cool the host fluid running through the device, if desired.

Figure 9:
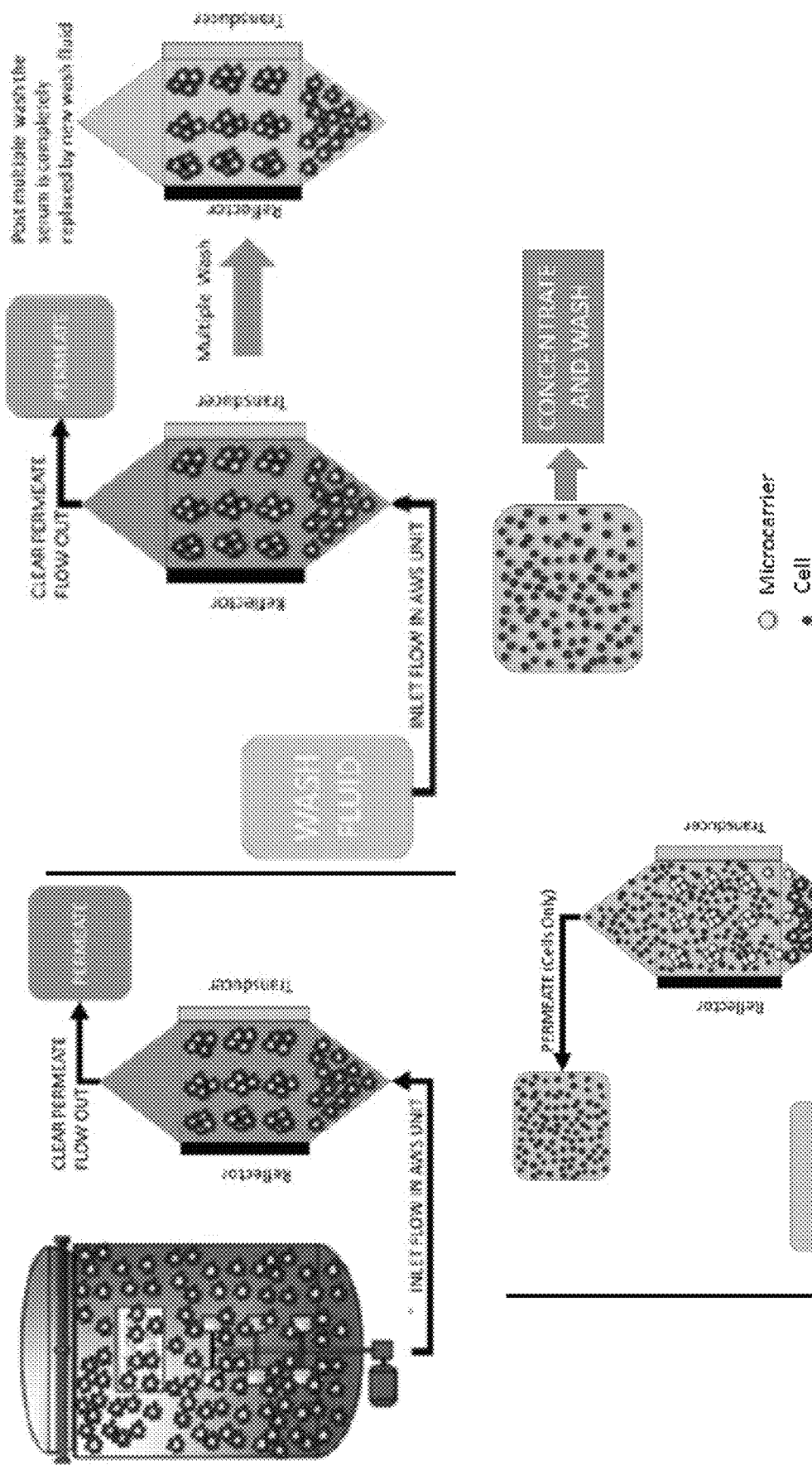
FIG. 9 is a block diagram illustrating affinity processes.

FIG. 9 illustrates a four-step process (with an optional fifth step) for concentrating, washing, and separating microcarriers from cells. The first step in the process involves concentrating the microcarriers with attached cells in an acoustophoretic device, such as those described herein. The microcarriers and attached cells can be introduced to the acoustophoretic device by receiving the microcarriers with attached cells from a bioreactor. In the bioreactor, the microcarriers and cells are suspended in a first media (e.g., growth serum or preservative material used to keep the cells viable in the bioreactor). The microcarriers with attached cells surrounded by the first media are concentrated by the acoustic standing wave(s) generated in the acoustophoretic device. In a second step, the concentrated microcarriers with attached cells are then washed with a second media to remove the first media (e.g., bioreactor growth serum or preservative material). The third step is to then introduce a third media containing an enzyme into the acoustophoretic device to detach the cells from the microcarriers through enzymatic action of the second media. In particular embodiments, trypsin is the enzyme used to enzymatically detach the cells from the microcarriers. The multi-dimensional acoustic standing wave can then be used to separate the cells from the microcarriers. Usually, this is done by trapping the microcarriers in the multi-dimensional acoustic standing wave, while the detached cells pass through with the third media. However, the cells can be trapped instead, if desired. Finally, the separated cells may optionally be concentrated and washed again, as desired.

After being concentrated and trapped/held in the multi-dimensional acoustic standing wave, the microcarriers can coalesce, clump, aggregate, agglomerate, and/or cluster to a critical size at which point the microcarriers fall out of the acoustic standing wave due to enhanced gravitational settling. The microcarriers can fall into a collector of the acoustophoretic device located below the acoustic standing wave, to be removed from the flow chamber.

During testing, steps one and two of concentration and washing, respectively, were performed using red and blue food dye to make colored fluid. The concentration mixture included SoloHill microcarriers in red fluid. The wash mixture included blue fluid and was passed through the device three times. The concentrate was observed under a microscope. The concentration step was shown to have a 99% efficiency. The first media (dyed red) was progressively washed out by a second media (dyed blue) over a series of wash passes. The light absorbance data is shown in Table 5 below.

TABLE 5

| | Light Absorbance | |
| --- | --- | --- |
| Sample | Red (510 nm) | Blue (630 nm) |
| Feed | 0.138 | 0.041 |
| Wash Pass 1 | 0.080 | 0.066 |
| Wash Pass 2 | 0.063 | 0.080 |
| Wash Pass 3 | 0.054 | 0.084 |

The decrease in red light absorbance and increase in blue light absorbance evidences the feasibility of the washing steps. The testing of the acoustophoretic concentrating, washing, and separating process showed that the process is appropriate for cell therapy and microcarrier applications. The concentrate and wash steps were performed with a resulting efficiency of greater than 99%, and the separating step e.g., separating the cells from the microcarriers, was performed with greater than 98% efficiency.

In an example implementation, a concentrate-wash process was employed with a volume of 750 mL, 1.5 billion cells, prior to electroporation. A parallel example implementation had a volume of 5 L and 150 billion cells prior to electroporation. Table 6 summarizes the results for each example.

TABLE 6

| Item | Baseline | Preferred |
| --- | --- | --- |
| Initial volume | 750 mL (3.75 L) | |
| Final volume | 10-25 mL (50-125 mL) | |
| Total viable cells | 1-1.5 B (5-7.5 B) | |
| Viable cell recovery | 80% | >80% |

In an example implementation, a concentrate-wash process was employed with a volume of 1 L, 30 billion cells, post cell expansion. A parallel example implementation had a volume of 5 L and 150 billion cells post cell expansion. Table 7 summarizes the results for each of these examples.

TABLE 7

| Item | Baseline | Preferred |
| --- | --- | --- |
| Initial volume | 1 L (5 L) | |
| Final volume (flexible if FDS owns next stage of the process) | 100-200 mL (500-1000 mL) | |
| Total viable cells | 30 B (150 B) | |
| Viable cell recovery | 80% | >90% |

Figure 10:
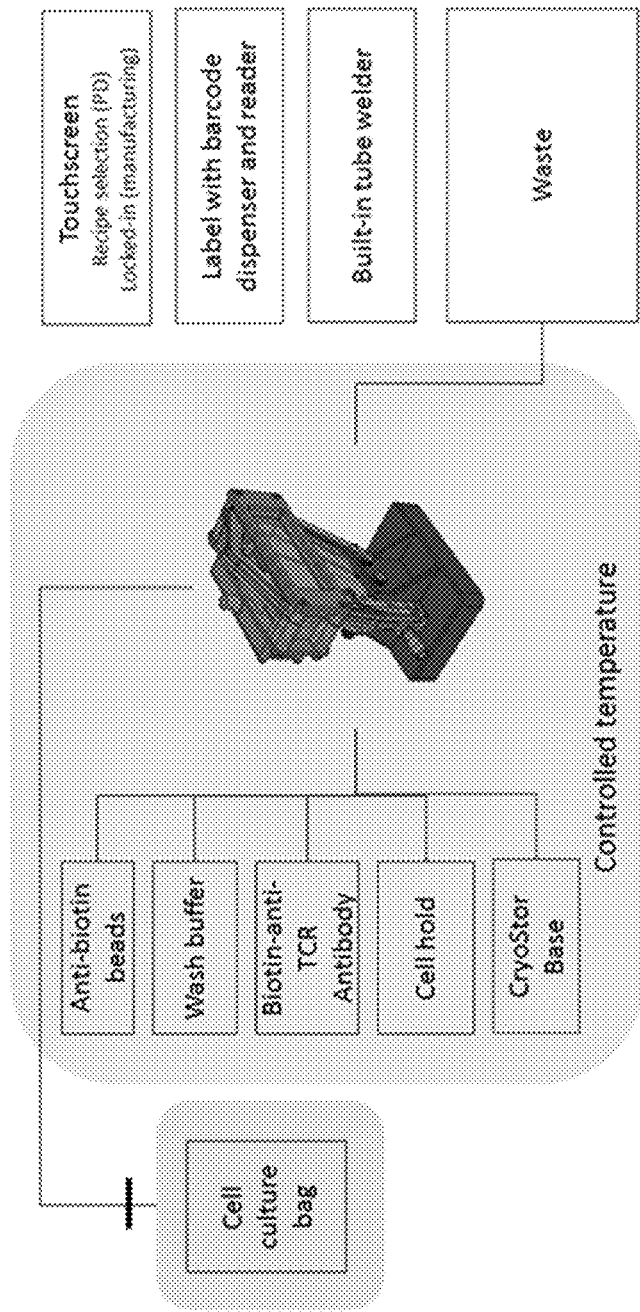
FIG. 10 is a block diagram illustrating an integrated concentrate-wash-cell selection device.

As discussed above, one or more processes in the systems for production of cell therapy products may be integrated in a single device. Referring to FIG. 10, a block diagram of a device suitable for implementing a concentrate-wash process and a cell selection process is illustrated. The illustrated device is capable of mixing and separation operations. A cell culture bag can be loaded into the device for the application of various processes. The cell culture bag includes various ports for fluidic input and/or output. The device provides an acoustic field that can retain cells and/or particles such as beads to implement an affinity selection process, a concentration process and/or a wash process. In some examples, mechanisms are provided to control the inputs, outputs and operations of the device to permit one or more processes to be automated. The automation implementation includes a controller that can operate pumps, valves, ultrasonic transducers, and other equipment used to implement the above noted processes. The automation implementation includes a user interface that's displays information related to various processes, and can accept input for a selection of parameters and/or process steps. The user interface may also provide statistical or process status data.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known processes, structures, and techniques have been shown without unnecessary detail to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional stages or functions not included in the figure.

Having described several example configurations, various modifications, alternative constructions, and equivalents may be used without departing from the spirit of the disclosure. For example, the above elements may be components of a larger system, wherein other structures or processes may take precedence over or otherwise modify the application of the invention. Also, a number of operations may be undertaken before, during, or after the above elements are considered. It is intended that the present disclosure be construed as including all such modifications and alterations insofar as they come within the scope of the appended claims or the equivalents thereof.

The invention claimed is:

1. A system for producing a therapeutic by implementing a series of processes, the system comprising:
    a user interface for accepting a user input for process selection;
    a cell processing device for performing a process on a cell suspension to obtain a processed cell suspension;
    an acoustic device fluidly connected to the cell processing device with a closed connection and being configured to selectively implement a concentrate process, a washing process or an affinity selection process on the cell suspension or on the processed cell suspension, wherein the acoustic device includes an ultrasonic transducer configured to generate an acoustic wave to retain cellular material or a structure to which the cellular material is bound;

a chamber in the acoustic device for receiving the cellular material or a structure to which the cellular material is bound, the ultrasonic transducer being coupled to the chamber;

at least a portion of the chamber near the ultrasonic transducer being vertically oriented;

a valve coupled to the chamber for controlling fluid flow into or out of the chamber; and a controller coupled to the user interface, the valve and the ultrasonic transducer and configured to control the valve and the ultrasonic transducer to implement a selected concentrate process, washing process or affinity selection process based on the user input.

2. The system of claim 1, further comprising an angled wave acoustic device for fractionating the cellular material.

3. The system of claim 2, wherein the angled wave acoustic device is configured to receive cellular material that is included in an apheresis product.

4. The system of claim 1, wherein the acoustic device further comprises a recirculation path.

5. The system of claim 1, further comprising a bag coupled to the chamber.

6. The system of claim 1, further comprising a closed system.

7. The system of claim 1, wherein the affinity selection process includes negative selection for TCR+cells.

8. The system of claim 1, further comprising another acoustic device fluidly coupled to the acoustic device to form a closed end-to-end CAR T production process.

9. A cell therapy production system, comprising:

a user configured to accept a user input for process selection;

a number of fluidly interconnected devices that form a closed system, at least one of the devices being a cell processing device for performing a process on a cell suspension to obtain a processed cell suspension, and at least another one of the devices being an acoustic device configured to retain cells or structures for supporting cells in the cell suspension or in the processed cell suspension;

the acoustic device including an ultrasonic transducer coupled to a vertically oriented chamber through which the cell suspension or the processed cell suspension is flowed; and a controller coupled to the user interface and the acoustic device and configured to control the acoustic device to implement a concentrate process, a washing process or an affinity selection process based on the user input.

10. The system of claim 9, wherein the devices form and end-to-end cell therapy production system.

* * * * *